United States Patent
Ainekulu et al.

(10) Patent No.: US 12,162,951 B2
(45) Date of Patent: Dec. 10, 2024

(54) ANTI-IDIOTYPIC ANTIBODIES AGAINST ANTI-KLK2 ANTIBODIES

(71) Applicant: Janssen Biotech, Inc., Horsham, PA (US)

(72) Inventors: Zemeda Ainekulu, San Diego, CA (US); Qiang Chen, San Diego, CA (US); Ellen Chi, Del Mar, CA (US); Wilson Edwards, Cardiff by the Sea, CA (US); Matt Husovsky, Ramona, CA (US); Ann Lacombe, San Diego, CA (US); Quynh Nguyen, San Diego, CA (US); Paul H. Kim, Encinitas, CA (US); H. Mimi Zhou, San Diego, CA (US); John T. Lee, Ambler, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/376,830

(22) Filed: Jul. 15, 2021

(65) Prior Publication Data

US 2022/0064334 A1    Mar. 3, 2022

Related U.S. Application Data

(60) Provisional application No. 63/053,275, filed on Jul. 17, 2020.

(51) Int. Cl.
| | | |
|---|---|---|
| *G01N 33/53* | (2006.01) | |
| *C07H 21/04* | (2006.01) | |
| *C07K 1/22* | (2006.01) | |
| *C07K 16/42* | (2006.01) | |
| *C12N 5/02* | (2006.01) | |
| *C12N 15/00* | (2006.01) | |
| *C12P 21/06* | (2006.01) | |
| *G01N 33/68* | (2006.01) | |

(52) U.S. Cl.
CPC ........... *C07K 16/4241* (2013.01); *C07K 1/22* (2013.01); *G01N 33/6854* (2013.01); *C07K 2317/20* (2013.01); *C07K 2317/21* (2013.01); *C07K 2317/24* (2013.01); *C07K 2317/33* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 4,873,191 A | 10/1989 | Wagner et al. |
| 5,175,384 A | 12/1992 | Krimpenfort et al. |
| 5,545,806 A | 8/1996 | Lonberg et al. |
| 5,569,825 A | 10/1996 | Lonberg et al. |
| 5,602,299 A | 2/1997 | Lazzarini |
| 5,714,352 A | 2/1998 | Jakobovits |
| 6,037,521 A | 3/2000 | Sato et al. |
| 6,066,778 A | 3/2000 | Ginsburg et al. |
| 6,265,150 B1 | 7/2001 | Terstappen et al. |
| 2002/0197266 A1 | 2/2002 | Debinski |
| 2007/0004909 A1 | 1/2007 | Johnson et al. |
| 2009/0060910 A1 | 3/2009 | Johnson et al. |
| 2010/0021477 A1 | 1/2010 | Tsui et al. |
| 2018/0326102 A1 | 11/2018 | Ulmert |

FOREIGN PATENT DOCUMENTS

| | | | |
|---|---|---|---|
| WO | WO90/08832 | 8/1990 | |
| WO | WO93/03769 | 3/1993 | |
| WO | WO93/19191 | 9/1993 | |
| WO | WO94/12649 | 6/1994 | |
| WO | WO94/28938 | 12/1994 | |
| WO | WO95/00655 | 1/1995 | |
| WO | WO95/11984 | 5/1995 | |
| WO | WO 2005/075662 A2 | 8/2005 | |
| WO | WO 2009/085462 A1 | 7/2009 | |
| WO | WO2010/017257 | 2/2010 | |
| WO | WO 2015/075445 A1 | 5/2015 | |
| WO | WO-2018023100 A2 * | 2/2018 | ......... C07K 16/2803 |
| WO | WO 2021/019389 A1 | 2/2021 | |

OTHER PUBLICATIONS

Thomson (IgG Structure and Function, Editor(s): Michael J.H. Ratcliffe, Encyclopedia of Immunobiology, Academic Press, 2016, p. 1). (Year: 2016).*
Jena et al. Chimeric Antigen Receptor (CAR)-Specific Monoclonal Antibody to Detect CD19-Specific T Cells in Clinical Trials PLoS One. 2013;8(3):e57838. (Year: 2013).*
Edwards et al., The remarkable flexibility of the human antibody repertoire; isolation of over one thousand different antibodies to a single protein, BLyS. J Mol Biol. Nov. 14, 2003;334(1): 103-18. (Year: 2003).*
Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*
Goel et al., Plasticity within the antigen-combining site may manifest as molecular mimicry in the humoral immune response. J Immunol. Dec. 15, 2004; 173(12):7358-67. (Year: 2004).*

(Continued)

*Primary Examiner* — Maher M Haddad

(57) ABSTRACT

In certain aspects, the disclosure relates to anti-idiotype antibodies and antigen-binding portions thereof that specifically bind a KL2B413 containing protein, e.g., an antibody or antigen-binding portions thereof. In some aspects, the anti-idiotype antibodies and antigen-binding portions of the present disclosure can be used in methods to detect and quantify cells expressing chimeric antigen receptors that include KL2B413.

29 Claims, 7 Drawing Sheets

Specification includes a Sequence Listing.

(56) References Cited

OTHER PUBLICATIONS

Kanyavuz et al., Breaking the law: unconventional strategies for antibody diversification. Nat Rev Immunol. Jun. 2019; 19(6):355-368. (Year: 2019).*

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*

Cheadle, E.J., et al., "Chimeric Antigen Receptors for T-Cell Based Therapy", (2012), Methods in Molecular Biology, vol. 907, pp. 645-666.

Wu, T.T., et al., "An Analysis of the Sequences of the Variable Regions of Bence Jones Proteins and Myeloma Light Chains and Their Implications for Anti-body Complementarity", (1970), J. Exp. Med. 132, pp. 211-250.

Chothia, C., et al., "Canonical Structures for the Hypervariable Regions of Immunoglobulins", (1987), J. Mol. Biol., vol. 196, pp. 901-917.

Lefranc, M.P., et al., "IMGT unique numbering for immunoglobulin and T cell receptor variable domains and Ig superfamily V-like domains", (2003), Development and Comparative Immunology, vol. 27, pp. 55-77.

Knappik, A., et al., "Fully Synthetic Human Combinatorial Antibody Libraries (HuCAL) Based on Modular Consensus Frameworks and CDRs Randomized with Trinucleotides", J. Mol. Biol., (2000), vol. 296, pp. 57-86.

Shi, L., et al., "De Novo Selection of High-Affinity Antibodies from Synthetic Fab Libraries Displayed on Phage as pIX Fusion Proteins", J. Mol. Biol., (2010), vol. 397, pp. 385-396.

Kohler, G., et al., "Derivation of specific antibody-producing tissue culture and tumor lines by cell fusion", (1976), Eur. J. Immunol., vol. 6, pp. 511-519.

Haskard, D.O., et al., The Production of Human Monoclonal Autoantibodies from Patients with Rheumatoid Arthritis by the EBV-Hybridoma Technique, (1984), Journal of Immunological Methods, vol. 74, pp. 361-367.

Roder, J.C., et al., "The EBV-Hybridoma Technique", (1986), The Methods of Enzymology, vol. 121, pp. 140-167.

Huse, W.D., et al., "Generation of a Large Combinatorial Library of the Immunoglobulin Repertoire in Phage Lambda", (1989), Science, vol. 246, pp. 1275-1281.

Tatusova, T.A., et al., "Blast 2 Sequences, a new tool for comparing protein and nucleotide sequences", (1999), FEMS Microbiology Letters, vol. 174, pp. 247-250.

International Search Report from PCT/IB2021/056417 dated Oct. 14, 2021.

Ali, R.R., et al., "Gene transfer into the mouse retina mediated by an adeno-associated viral vector", (1996), Human Molecular Genetics, vol. 5, No. 5, pp. 591-594.

Amoah, E.A., et al., "Biotechnological Advances in Goat Reproduction", (1997), J. Anim. Sci., vol. 75, pp. 578-585.

Bennett, J., et al., "Real-Time, Noninvasive In Vivo Assessment of Adeno-Associated Virus-Mediated Retinal Transduction", (1997), Invest Opthalmol. Vis. Sci., vol. 38, No. 13, pp. 2857-2863.

Bradley, A., et al., "Formation of germ-line chimaeras from embryo-derived teratocarcinoma cell lines", (1984), Nature, vol. 309, pp. 255-258.

Brinster, R.L., et al., "Factors affecting the efficiency of introducing foreign DNA into mice by microinjecting eggs", (1985), Proc. Natl. Acad. Sci. USA, vol. 82, pp. 4438-4442.

Cunningham, D., et al., "In vitro and in vivo model systems used in prostate cancer research", (2015), J. Biol Methods, vol. 2, No. 1, p. e17.

Evans, M.J., et al., "Establishment in culture of pluripotential cells from mouse embryos", (1981), Nature, vol. 292, pp. 154-156.

Flannery, J.G., et al., "Efficient photoreceptor-targeted gene expression in vivo by recombinant adeno-associated virus", (1997), Proc. Natl. Acad. Sci. USA, vol. 94, pp. 6916-6921.

Flotte, T.R., et al., "Stable in vivo expression of the cystic fibrosis transmembrane conductance regulator with an adeno-associated virus vector", (1993), Proc. Natl. Acad. Sci. USA, vol. 90, pp. 10613-10617.

Gossler, A., et al., "Transgenesis by means of blastocyst-derived embryonic stem cell lines", (1986), Proc. Natl. Acad. Sci. USA, vol. 83, pp. 9065-9069.

Hekim, C., et al., "Novel Peptide Inhibitors of Human Kallikrein 2", (2006), Journal of Biological Chemistry, vol. 281, No. 18, pp. 12555-12560.

International Search Report from PCT/IB2022/055355 mailed Oct. 11, 2022.

Houdebine, LM., "The production of pharmaceutical protein from the milk of transgenic animals", (1995), Reprod Nutr Dev, vol. 35, pp. 609-617.

Jaenisch, R., "Transgenic Animals", (1988), Science, vol. 240, pp. 1468-1474.

Jaenisch, R., "Germ line integration and Mendelian transmission of the exogenous Moloney leukemia virus", (1976), Proc. Natl. Acad. Sci. USA, vol. 73, No. 4, pp. 1260-1264.

Jahner, D., "Insertion of the bacterial gpt gene into the germ line of mice by retroviral infection", (1985), Proc. Natl. Acad. Sci. USA, vol. 82, pp. 6927-6931.

Jomary, C., et al., "Rescue of photoreceptor function by AAV-mediated gene transfer in a mouse model of inherited retinal degeneration", (1997), Gene Therapy, vol. 4, pp. 683-690.

Kim, J.H., et al., "Development of a Positive Method for Male Stem Cell-Mediated Gene Transfer in Mouse and Pig", (1997), Mol. Reprod. Dev., vol. 46, No. 4, pp. 515-526.

Kinoshita, T., "Glycosylphosphatidylinositol (GPIO Anchors: Biochemistry and Cell Biology: Introduction to a Thematic Review Series", (2016), J. Lipid Res., vol. 57, No. 1, pp. 4-5.

Korenchuk, S., et al., "VCaP, A Cell-Based Model System of Human Prostate Cancer", (2001), In Vivo, vol. 15, No. 2, pp. 163-168.

Lavitrano, M., et al., "Sperm Cells as Vectors for Introducing Foreign DNA into Eggs: Genetic Transformation of Mice", (1989), Cell, vol. 57, pp. 717-723.

Litke, J.L., et al., "Highly efficient expression of circular RNA aptamers in cells using autocatalytic transcripts", (2019), Nature Biotechnol., vol. 37, No. 6, pp. 667-675.

Lo, C.W., "Transformation by Iontophoretic Microinjection of DNA: Multiple Integrations Without Tandem Insertions", (1983), Mol. Cell. Biol., vol. 3, No. 10, pp. 1803-1814.

Medof, M.E., et al., "Cell-surface engineering with GPI-anchored proteins", (1996), Faseb J., vol. 10, No. 5, pp. 574-586.

Mendelson, E., et al., "Expression and Rescue of a Nonselected Marker from an Integrated AAV Vector", (1988), Virol., vol. 166, pp. 154-165.

Miyagishi, M., et al., "U6 promoter-driven siRNAs with four uridine 3'overhangs efficiently suppress targeted gene expression in mammalian cells", (2002), Nature Biotechnol., vol. 19, pp. 497-500.

Miyoshi, H., et al., "Stable and efficient gene transfer into the retina using an HIV- based lentiviral vector", (1997), Proc. Natl. Acad. Sci. USA, vol. 94, pp. 10319-10323.

Nasser, N.J., et al., "Human tissue Kallikreins: Blood levels and response to radiotherapy in intermediate risk prostate cancer", (2017), Radiother. Oncol., vol. 124, No. 3, pp. 427-432.

Obiezu, C.V., et al., "Human tissue kallikrein gene family: application in cancer", (2005), Cancer Letters, vol. 224, pp. 1-22.

Paulick, M.G., et al., "The Glycosylphosphatidylinositol Anchor: A Complex Membrane-Anchoring Structure for Proteins", (2008), Biochemistry, vol. 47, pp. 6991-7000.

Petters, R.M., "Transgenic Livestock as Genetic Models of Human Disease", (1994), Reprod. Fertil. Dev., vol. 6, No. 5, pp. 643-645.

Pierleoni, A., et al., "PredGPI: a GPI-anchor predictor", (2008), BMC Bioinformatics, vol. 9, pp. 1-11.

Putten, H.V.D., et al., "Efficient insertion of genes into the mouse germ line via retroviral vectors", (1985), Proc. Natl. Acad. Sci. USA, vol. 82, pp. 6148-6152.

(56) References Cited

OTHER PUBLICATIONS

Robertson, E., et al., "Germ-line transmission of genes introduced into cultured pluripotential cells by retroviral vector", (1986), Nature, vol. 323, pp. 445-448.

Rolling, F., et al., "Evaluation of Adeno-Associated Virus-Mediated Gene Transfer into the Rat Retina by Clinical Fluorescence Photography", (1999), Human Gene Therapy, vol. 10, pp. 641-648.

Samulski, R.J., et al., "Helper-Free Stocks of Recombinant Adeno-Associated Viruses: Normal Integration Does Not Require Viral Gene Expression", (1989), Journal of Virology, vol. 63, No. 9, pp. 3822-3828.

Schnieke, A.E., et al., "Human Factor IX Transgenic Sheep Produced by Transfer of Nuclei from Transfected Fetal Fibroblasts", (1997), Science, vol. 278, No. 5346, pp. 2130-2133.

Smith, R., et al., "Enzalutamide response in a panel of prostate cancer cell lines reveals a role for glucocorticoid receptor in enzalutamide resistant disease", (2020), Scientific Reports, vol. 10, No. 1, pp. 1-13.

Thompson, S., et al., "Germ Line Transmission and Expression of a Corrected HPRT Gene Produced by Gene Targeting in Embryonic Stem Cells", (1989), Cell, vol. 56, pp. 313-321.

Thorek, D.L.J., et al., "Prostate-specific kallikrein-related peptidases and their relation to prostate cancer biology and detection", (2013), Thromb Haemost, vol. 110, pp. 484-492.

Xia, X.G., et al., "An enhanced U6 promoter for synthesis of short hairpin RNA", (2003), Nucleic Acids Research, vol. 31, No. 17, page e100.

\* cited by examiner

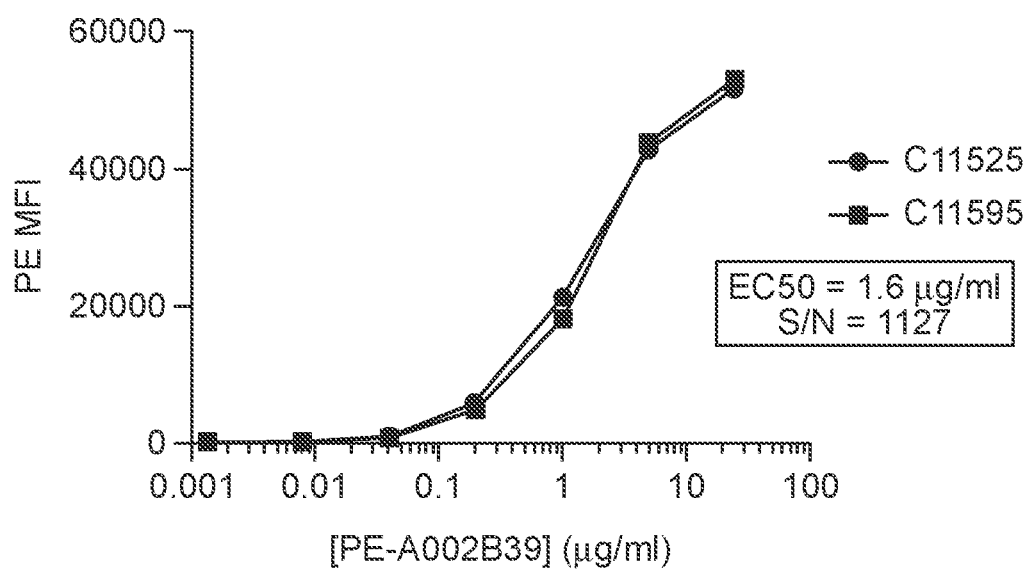

SEQUENCE LISTING

```
<160> NUMBER OF SEQ ID NOS: 48

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser
            20                  25                  30
```

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe
            20                  25
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Gly Gly Thr Phe Ser Ser Tyr
1               5
```

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Gly Gly Thr Phe Ser Ser Tyr Ala Ile Ser
1               5                   10
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Ser Tyr Ala Ile Ser
1               5
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Ser Ser Tyr Ala Ile Ser
1               5
```

<210> SEQ ID NO 8
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ile Ser Trp Val Arg Gln Ala Pro Gly Gln Gly Leu Glu Trp Met
1               5                   10                  15

Gly Gly Ile

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Val Arg Gln Ala Pro Gly Gln Gly Leu Glu Trp Met Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Val Arg Gln Ala Pro Gly Gln Gly Leu Glu
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Pro Ile Phe Gly Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Ile Pro Ile Phe Gly Thr Ala Asn
1               5                   10

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13
```

```
Gly Ile Ile Pro Ile Phe Gly Thr Ala Asn Tyr Ala Gln Lys Phe Gln
1               5                   10                  15

Gly

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Met Gly Gly Ile Ile Pro Ile Phe Gly Thr Ala Asn
1               5                   10

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Asn Tyr Ala Gln Lys Phe Gln Gly Arg Val Thr Ile Thr Ala Asp
1               5                   10                  15

Glu Ser Thr Ser Thr Ala Tyr Met Glu Leu Ser Ser Leu Arg Ser Glu
                20                  25                  30

Asp Thr Ala Val Tyr Tyr Cys Ala Arg
        35                  40

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Tyr Ala Gln Lys Phe Gln Gly Arg Val Thr Ile Thr Ala Asp Glu Ser
1               5                   10                  15

Thr Ser Thr Ala Tyr Met Glu Leu Ser Ser Leu Arg Ser Glu Asp Thr
                20                  25                  30

Ala Val Tyr Tyr Cys Ala Arg
        35

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 18
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Tyr Ala Gln Lys Phe Gln Gly Arg Val Thr Ile Thr Ala Asp Glu Ser
1               5                   10                  15
Thr Ser Thr Ala Tyr Met Glu Leu Ser Ser Leu Arg Ser Glu Asp Thr
            20                  25                  30
Ala Val Tyr Tyr Cys
        35

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Gln Trp Gly Leu Asp Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Val Gln Trp Gly Leu Asp
1               5

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Gly Gln Gly Thr Leu Val Thr Val Ser Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Trp Gly Gln Gly Thr Leu Val Thr Val Ser Ser
1               5                   10

<210> SEQ ID NO 23
<211> LENGTH: 23
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val
            20                  25

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Ala Ser Gln Ser Val Asp Ser Ala Leu Ala
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Ser Ala Leu Ala Trp Tyr
1               5

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Tyr Gln Gln Lys Pro Gly Gln Ala Pro Arg Leu Leu Ile Tyr
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 28

Gln Gln Lys Pro Gly Gln Ala Pro Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Ser Asn Arg Ala Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Leu Ile Tyr Gly Ala Ser Asn Arg Ala
1               5                   10

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Thr Gly Ile Pro Ala Arg Phe Ser Gly Ser Gly Ser Gly Thr Asp Phe
1               5                   10                  15

Thr Leu Thr Ile Ser Ser Leu Glu Pro Glu Asp Phe Ala Val Tyr Tyr
            20                  25                  30

Cys

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Arg Phe Asn Trp Pro Ile Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Arg Phe Asn Trp Pro Ile
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Phe Gly Gln Gly Thr Lys Val Glu Ile Lys
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Gly Gln Gly Thr Lys Val Glu Ile Lys
1               5                   10

<210> SEQ ID NO 37
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gln Trp Gly Leu Asp Tyr Trp Gly Gln Gly Thr Leu Val
            100                 105                 110

```
Thr Val Ser Ser Ala Lys Thr Thr Ala Pro Ser Val Tyr Pro Leu Ala
            115                 120                 125

Pro Val Cys Gly Asp Thr Thr Gly Ser Ser Val Thr Leu Gly Cys Leu
        130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 38
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gaagtgcagc tggtgcagag cggcgcggaa gtgaaaaaac cgggcagcag cgtgaaagtg      60
agctgcaaag cgagcggcgg cacctttagc agctatgcga ttagctgggt gcgccaggcg     120
ccgggccagg gcctggaatg gatgggcggc attattccga ttttggcac cgcgaactat      180
```

-continued

```
gcgcagaaat tcagggccg cgtgaccatt accgcggatg aaagcaccag caccgcgtat      240
atggaactga gcagcctgcg cagcgaagat accgcggtgt attattgcgc gcgcgtgcag      300
tggggcttgg actattgggg ccagggcacc ctggtgaccg tgagcagcgc caaaacaaca      360
gcaccaagtg tctatccact ggcccctgtg tgtggagata caactggctc ctcggtgact      420
ctaggatgcc tggtcaaggg ttatttccct gagccagtga ccttgacctg gaactctgga      480
tccctgtcca gtggtgtgca caccttccca gctgtcctgc agtctgacct ctacaccctc      540
agcagctcag tgactgtaac ctcgagcacc tggcccagcc agtccatcac ctgcaatgtg      600
gcccacccgg caagcagcac caaggtggac aagaaaattg agcccagagg ccccacaatc      660
aagccctgtc ctccatgcaa atgcccagca cctaacctct gggtggacc atccgtcttc      720 atcttccctc caaagatcaa ggatgtactc atgatctccc tgagccccat agtcacatgt      780
gtggtggtgg atgtgagcga ggatgaccca gatgtccaga tcagctggtt tgtgaacaac      840
gtggaagtac acacagctca gacacaaacc catagagagg attacaacag tactctccgg      900
gtggtcagtg ccctccccat ccagcaccag gactggatga gtggcaagga gttcaaatgc      960
aaggtcaaca acaaagacct cccagcgccc atcgagagaa ccatctcaaa acccaaaggg     1020
tcagtaagag ctccacaggt atatgtcttg cctccaccag aagaagagat gactaagaaa     1080
caggtcactc tgacctgcat ggtcacagac ttcatgcctg aagacattta cgtggagtgg     1140
accaacaacg ggaaaacaga gctaaactac aagaacactg aaccagtcct ggactctgat     1200
ggttcttact tcatgtacag caagctgaga gtggaaaaga gaactgggt ggaaagaaat     1260 agctactcct gttcagtggt ccacgagggt ctgcacaatc accacgac taagagcttc     1320 tcccggactc cgggtaaa                                                   1338
```

<210> SEQ ID NO 39
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Ala
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Asn Trp Pro Ile
                85                  90                  95

Thr Phe Gly Gln Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140
```

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
        180                 185                 190

Thr Cys Glu Ala Thr His Lys Thr Ser Thr Ser Pro Ile Val Lys Ser
    195                 200                 205

Phe Asn Arg Asn Glu Cys
    210

<210> SEQ ID NO 40
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
gaaattgtgc tgacccagag cccggcgacc ctgagcctga gcccgggcga acgcgcgacc      60
cttagctgcc gtgcaagtca gagtgtggac agcgcgctgg cgtggtatca gcagaaaccg     120
ggccaggcgc cgcgcctgct gatttatggt gcgagcaacc gcgcgaccgg cattccggcg     180
cgctttagcg gcagcggcag cggcaccgat tttaccctga ccattagcag cctggaaccg     240
gaagattttg cggtgtatta ttgccagcag cgtttcaact ggccgatcac ctttggccag     300
ggcaccaaag tggaaattaa acgggctgat gctgcaccga ctgtgtccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gt                        642

<210> SEQ ID NO 41
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

```
Val Trp Gly Gln Gly Thr Thr Val Thr Val Ser Ser
        115                 120

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Arg
                85                  90                  95

Thr Phe Gly Gln Gly Thr Lys Val Glu Ile Lys
            100                 105

<210> SEQ ID NO 43
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asn Tyr Asp Ile Leu Thr Gly His Tyr Gly Met Asp
            100                 105                 110

Val Trp Gly Gln Gly Thr Thr Val Thr Val Ser Ser Gly Gly Ser Glu
        115                 120                 125

Gly Lys Ser Ser Gly Ser Gly Ser Glu Ser Lys Ser Thr Gly Gly Ser
    130                 135                 140

Glu Ile Val Leu Thr Gln Ser Pro Ser Phe Leu Ser Ala Ser Val Gly
145                 150                 155                 160

Asp Arg Val Thr Ile Thr Cys Arg Ala Ser Gln Gly Ile Ser Ser Tyr
                165                 170                 175
```

Leu Ser Trp Tyr Gln Gln Lys Pro Gly Lys Ala Pro Lys Leu Leu Ile
                180                 185                 190

Tyr Ala Thr Ser Thr Leu Gln Ser Gly Val Pro Ser Arg Phe Ser Gly
            195                 200                 205

Ser Gly Ser Gly Thr Glu Phe Thr Leu Thr Ile Ser Ser Leu Gln Pro
    210                 215                 220

Glu Asp Phe Ala Thr Tyr Tyr Cys Gln Gln Leu Asn Ser Tyr Pro Arg
225                 230                 235                 240

Thr Phe Gly Gln Gly Thr Lys Val Glu Ile Lys Ser Thr Pro Ala
                245                 250                 255

Pro Arg Pro Pro Thr Pro Ala Pro Thr Ile Ala Ser Gln Pro Leu Ser
                260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
    290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
    355                 360                 365

Ser Ala Asp Ala Pro Ala Tyr Lys Gln Gly Gln Asn Gln Leu Tyr Asn
370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
    435                 440                 445

Asp Gly Leu Tyr Gln Gly Leu Ser Thr Ala Thr Lys Asp Thr Tyr Asp
450                 455                 460

Ala Leu His Met Gln Ala Leu Pro Pro Arg
465                 470

<210> SEQ ID NO 44
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ser Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly

```
            50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95

Thr Phe Gly Gln Gly Thr Lys Val Glu Ile Lys Gly Gly Ser Glu Gly
            100                 105                 110

Lys Ser Ser Gly Ser Gly Ser Glu Ser Lys Ser Thr Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Thr Phe Ser Ser Tyr Trp
145                 150                 155                 160

Met Thr Trp Val Arg Gln Ala Pro Gly Lys Gly Leu Glu Trp Val Ala
                165                 170                 175

Asn Ile Lys Gln Asp Gly Ser Glu Arg Tyr Tyr Val Asp Ser Val Lys
            180                 185                 190

Gly Arg Phe Thr Ile Ser Arg Asp Asn Ala Lys Asn Ser Leu Tyr Leu
            195                 200                 205

Gln Met Asn Ser Leu Arg Ala Glu Asp Thr Ala Val Tyr Tyr Cys Ala
        210                 215                 220

Arg Asp Gln Asn Tyr Asp Ile Leu Thr Gly His Tyr Gly Met Asp Val
225                 230                 235                 240

Trp Gly Gln Gly Thr Thr Val Thr Val Ser Ser Thr Ser Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
        290                 295                 300

Gly Thr Cys Gly Val Leu Leu Leu Ser Leu Val Ile Thr Leu Tyr Cys
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
            355                 360                 365

Ser Ala Asp Ala Pro Ala Tyr Lys Gln Gly Gln Asn Gln Leu Tyr Asn
        370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
        450                 455                 460

Ala Leu His Met Gln Ala Leu Pro Pro Arg
465                 470
```

```
<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gln Trp Gly Leu Asp Tyr Trp Gly Gln Gly Thr Leu Val
            100                 105                 110

Thr Val Ser Ser
        115

```
<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Ala
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Asn Trp Pro Ile
                85                  90                  95

Thr Phe Gly Gln Gly Thr Lys Val Glu Ile Lys
            100                 105

```
<210> SEQ ID NO 47
<211> LENGTH: 261
<212> TYPE: PRT
<213> ORGANISM: Homo sapiens

<400> SEQUENCE: 47
```

Met Trp Asp Leu Val Leu Ser Ile Ala Leu Ser Val Gly Cys Thr Gly
1               5                   10                  15

```
Ala Val Pro Leu Ile Gln Ser Arg Ile Val Gly Gly Trp Glu Cys Glu
            20                  25                  30

Lys His Ser Gln Pro Trp Gln Val Ala Val Tyr Ser His Gly Trp Ala
        35                  40                  45

His Cys Gly Gly Val Leu Val His Pro Gln Trp Val Leu Thr Ala Ala
        50                  55                  60

His Cys Leu Lys Lys Asn Ser Gln Val Trp Leu Gly Arg His Asn Leu
65                  70                  75                  80

Phe Glu Pro Glu Asp Thr Gly Gln Arg Val Pro Val Ser His Ser Phe
                85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
            115                 120                 125

Pro Ala Lys Ile Thr Asp Val Val Lys Val Leu Gly Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
                180                 185                 190

Thr Glu Phe Met Leu Cys Ala Gly Leu Trp Thr Gly Gly Lys Asp Thr
            195                 200                 205

Cys Gly Gly Asp Ser Gly Gly Pro Leu Val Cys Asn Gly Val Leu Gln
210                 215                 220

Gly Ile Thr Ser Trp Gly Pro Glu Pro Cys Ala Leu Pro Glu Lys Pro
225                 230                 235                 240

Ala Val Tyr Thr Lys Val Val His Tyr Arg Lys Trp Ile Lys Asp Thr
            245                 250                 255

Ile Ala Ala Asn Pro
            260

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Ala Trp Val Trp Thr Leu Leu Phe Leu Met Ala Ala Ala Gln Ser
1               5                   10                  15

Ile Gln Ala
```

ANTI-IDIOTYPIC ANTIBODIES AGAINST ANTI-KLK2 ANTIBODIES

CROSS-REFERENCE TO RELATED APPLICATIONS

This application claims the benefit of U.S. Provisional Application Ser. No. 63/053,275, filed 17 Jul. 2020. The entire content of the aforementioned application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 7, 2021, is named JBI6351USNP1_SL.txt and is 35,146 bytes in size.

TECHNICAL FIELD

The invention relates to anti-idiotype antibodies and antigen-binding portions thereof that specifically bind a KL2B413 containing protein, e.g., an antibody or antigen-binding portions thereof. Methods to detect and quantify cells expressing chimeric antigen receptors that include KL2B413 are also provided.

BACKGROUND

Recent advances in the understanding of the delivery of genomic material and integration into a target's genome have great potential to transform the standard-of-care for a variety of diseases. T cell therapy utilizes isolated T cells that have been genetically modified to enhance their specificity for a specific tumor associated antigen. Genetic modification may involve the expression of a chimeric antigen receptor (CAR) or an exogenous T cell receptor to provide new antigen specificity onto the T cell. T cells expressing chimeric antigen receptors (CAR-T cells) can induce tumor immunoreactivity.

One particular CAR target of interest is Kallikrein related peptidase 2 (hK2, HK2), which is a trypsin-like enzyme with androgen receptor (AR)-driven expression specific to prostate tissue and prostate cancer. hK2 is activated by Transmembrane Protease, Serine 2 (TMPRSS2) and secreted into the ducts of the prostate, where it initiates a cascade that cleaves semenogelin, the extracellular matrix in ejaculate, to enhance sperm motility. hK2 expression is restricted to the prostate and prostate cancer tissue, however it has recently been demonstrated that hK2 was detectable in breast cancer lines and primary patient samples after appropriate activation of the AR-pathway by steroid hormones (U.S. Pat. Publ. No. 2018/0326102). Retrograde release of catalytically inactive hK2 into the blood occurs when the highly structured organization of the prostate is compromised upon hypertrophy or malignant transformation. Accordingly, there is a need for CAR-T cell therapies for treating prostate cancer. There is also a need for anti-idiotype antibodies directed to such CARs in order to detect, purify, or select proteins and cells expressing the CAR.

SUMMARY OF THE INVENTION

The disclosure provides anti-idiotype antibodies and antigen-binding portions thereof that specifically bind a KL2B413 containing protein, e.g., an antibody or antigen-binding portions thereof. The disclosure also provides nucleic acids encoding the anti-idiotype antibodies and antigen-binding portions thereof, methods of producing the anti-idiotype antibodies and antigen-binding portions thereof, methods of detecting KL2B413 (or cells expressing KL2B413) using the anti-idiotype antibodies and antigen-binding portions thereof and kits including the anti-idiotype antibodies and antigen-binding portions thereof.

In one aspect, the disclosure provides an anti-idiotype antibody or antigen-binding portion thereof that specifically binds an anti-hK2 target antibody, such as a target antibody that comprises KL2B413. In some embodiments, the target antibody or antigen-binding portion comprises a VH domain with an amino acid sequence comprising SEQ ID NOs:41 and a VL domain with an amino acid sequence comprising SEQ ID NOs:42.

In other embodiments, the anti-idiotype antibody or antigen-binding portion is for use in detecting KL2B413 in a biologic sample comprising: (a) providing a biological sample; (b) contacting the biological sample with the anti-idiotype antibody or antigen-binding portion; and (c) detecting the anti-idiotype antibody or antigen-binding portion.

In another aspect, the disclosure provides an anti-idiotype antibody or antigen-binding portion that specifically binds KL2B413 comprising a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprising a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34.

In some embodiments, the anti-idiotype antibody or antigen-binding portion thereof comprises a VH domain that has an amino acid sequence having at least 90% sequence identity to SEQ ID NO:45 and the VL domain has an amino acid sequence having at least 90% sequence identity to SEQ ID NO:46. In some embodiments, the anti-idiotype antibody or antigen-binding portion thereof comprises a heavy chain comprising an amino acid sequence having at least 90% sequence identity to SEQ ID NO: 37 and further comprises a light chain comprising an amino acid sequence having at least 90% sequence identity to SEQ ID NO:39. In some embodiments, the anti-idiotype antibody or antigen-binding portion thereof comprises a VH domain that has an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:45. In some embodiments, the anti-idiotype antibody or antigen-binding portion thereof comprises a VL domain that has an amino acid sequence having at least about 80%, 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:46.

In some embodiments, the anti-idiotype antibody or antigen-binding portion thereof comprises a VH domain that has an amino acid sequence of SEQ ID NO:45 and a VL domain that has an amino acid sequence of SEQ ID NO:46. In some other embodiments, the anti-idiotype antibody or antigen-binding portion thereof comprises a heavy chain comprising an amino acid sequence of SEQ ID NO:37 and further comprises a light chain comprising an amino acid sequence of SEQ ID NO:39.

In some embodiments, the antigen-binding portion is selected from a Fab, F(ab')$_2$, or scFv. In some embodiments, the antibody is a monoclonal antibody. In some embodiments, the antibody is a chimeric antibody. In some embodiments, the chimeric antibody comprises a murine IgG2a framework. In some other embodiments, the antibody is a fully human antibody. In some embodiments, the anti-idiotype antibody or antigen-binding portion thereof is specific to KL2B413, wherein KL2B413 is within the antigen-binding domain of the extracellular portion of a chimeric antigen receptor (CAR). In some embodiments, KL2B413 is an scFv and the anti-idiotype antibody or antigen-binding portion specifically binds an epitope in the scFv of the CAR. In some embodiments, KL2B413 specifically binds KLK2. In some embodiments, the antibody or antigen-binding portion does not cross-react to other KLK2 antibodies or other KLK2 binding CARs. In some embodiments, the CAR has an amino acid sequence selected from the group consisting of SEQ ID NOs: 43-44.

In some embodiments, the disclosure provides a nucleic acid encoding the heavy chain, the light chain, or both, of the anti-idiotype antibody or antigen-binding portion.

In another aspect, the disclosure provides a nucleic acid encoding the heavy chain, the light chain, or both, of an anti-idiotype antibody or an antigen-binding portion thereof that specifically binds KL2B413, wherein said nucleic acid comprises: the nucleotide sequence of SEQ ID NO: 38; the nucleotide sequence of SEQ ID NO: 40; or both. In another aspect, the disclosure provides a vector comprising the nucleic acid sequence. In some embodiments, the vector is an expression vector. In another aspect, the disclosure provides a host cell comprising the vector. In some embodiments, the host cell is a mammalian cell.

In another aspect, the disclosure provides a method of producing an anti-idiotype antibody or antigen-binding portion thereof that specifically binds KL2B413, said method comprising culturing a host cell under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture. In some embodiments, the host cell encodes a vector comprising a nucleic acid encoding the anti-idiotype antibody or antigen-binding portion thereof.

In another aspect, the disclosure provides a method for detecting KL2B413 in a biologic sample comprising: (a) providing a biological sample; (b) contacting the biological sample with the anti-idiotype antibody or antigen-binding portion; and (c) detecting the anti-idiotype antibody or antigen-binding portion.

In another aspect, the disclosure provides a method for detecting expression of a chimeric antigen receptor (CAR) comprising KL2B413 in a biologic sample comprising: (a) providing a biological sample; (b) contacting the biological sample with the anti-idiotype antibody or antigen-binding portion; and (c) detecting the anti-idiotype antibody or antigen-binding portion, and thereby detecting the expression of the CAR.

In some embodiments, the antibody comprises a detectable label. In some embodiments, the method further comprises further comprises contacting the anti-idiotype antibody or antigen-binding portion with a detectable label before detecting the anti-idiotype antibody or antigen-binding portion. In some embodiments, the biological sample is blood, serum or urine.

In some aspects, the disclosure provides a kit for detecting KL2B413 in a biologic sample comprising: (a) an anti-idiotype antibody or antigen-binding portion; and (b) instructions for detecting the anti-idiotype antibody or antigen-binding portion.

In other aspects, the disclosure provides a method of purifying KL2B413 from a sample comprising: (a) providing a biological sample comprising KL2B413; (b) contacting the biological sample with the anti-idiotype antibody or antigen-binding portion of the disclosure; and (c) capturing the anti-idiotype antibody or antigen-binding portion, and thereby purifying KL2B413.

In other aspects, the disclosure provides a method of selecting CAR-T cells from a cell population comprising: (a) providing a biological sample comprising CAR-T cells; (b) contacting the biological sample with an anti-idiotype antibody or antigen-binding portion; and (c) capturing the anti-idiotype antibody or antigen-binding portion, and thereby selecting CAR-T cells. In some embodiments, the anti-idiotype antibody or antigen-binding portion thereof is specific to KL2B413.

The disclosure contemplates all combinations of any of the foregoing aspects and embodiments, as well as combinations with any of the embodiments set forth in the detailed description and examples.

BRIEF DESCRIPTION OF THE DRAWINGS

For the purpose of illustrating the invention, there are depicted in the drawings certain embodiments of the disclosure. However, the disclosure is not limited to the precise arrangements and instrumentalities of the embodiments depicted in the drawings.

FIG. 7 shows a graphical representation of two different lots of PE-A002B39 that have similar binding profiles to KL2B413-LH-SupT1.

DETAILED DESCRIPTION OF THE INVENTION

Overview

Figure 1:
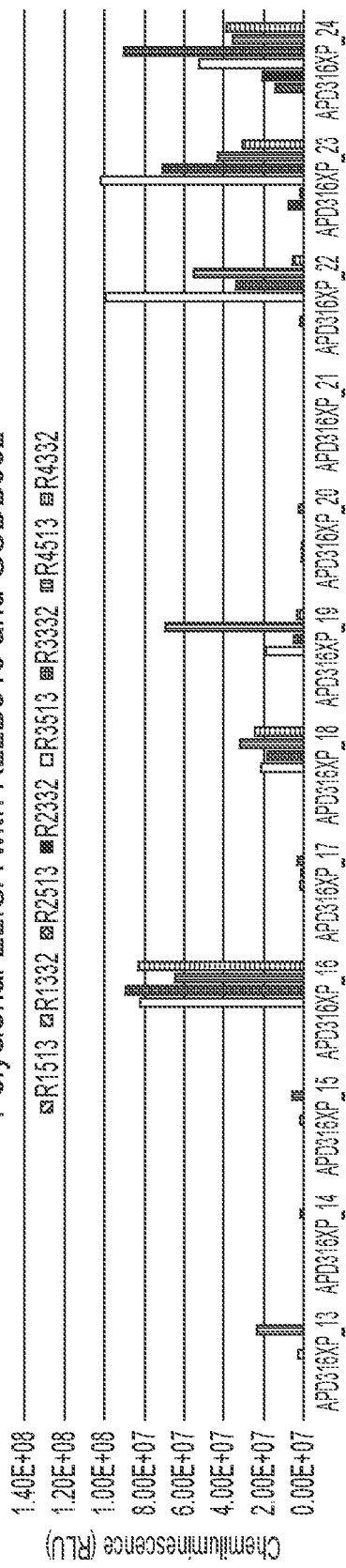
FIG. 1 shows a graphical representation of KL2B513 or KL2B610 specific binding enrichment after round four panning detected with Polyclonal ELISA.
Figure 1:
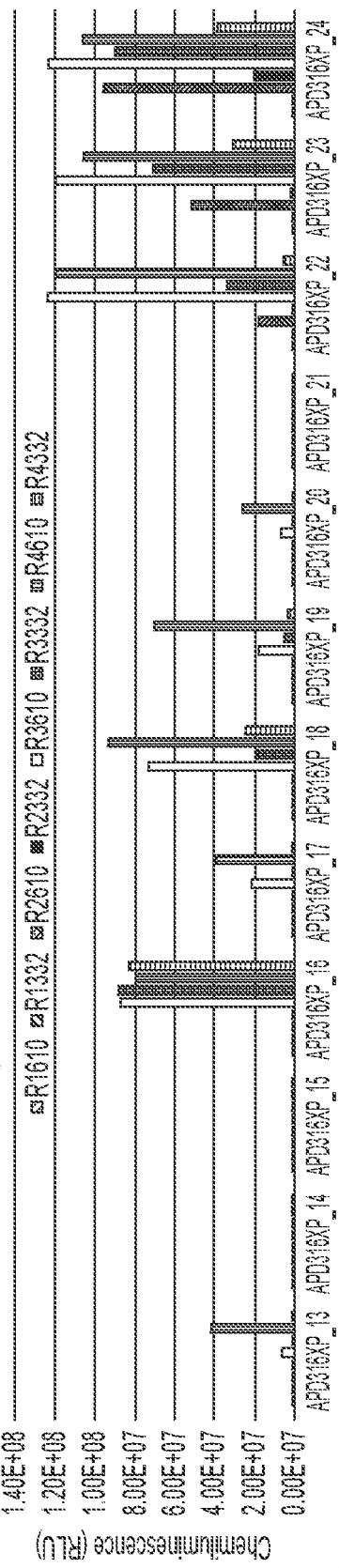

The disclosure provides anti-idiotype antibodies and antigen-binding portions thereof that specifically bind a KL2B413 containing protein, e.g., an antibody or antigen-binding portions thereof. The anti-idiotype antibodies and antigen-binding portions of the present disclosure can be used in methods to detect and quantify cells expressing CARs that include KL2B413. Such methods may allow a researcher to determine whether a given batch of in vitro generated CAR-T cells have expressed the desired CAR and thus whether the cells are therapeutically useful for targeting the desired proteins. In the present disclosure, the anti-idiotype antibodies and antigen-binding portions target KL2B413, which itself targets KLK2, a protein associated with prostatic tissue.

Definitions

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Activation" or "stimulation" or "activated" or "stimulated" refers to induction of a change in the biologic state of a cell resulting in expression of activation markers, cytokine production, proliferation or mediating cytotoxicity of target cells. Cells may be activated by primary stimulatory signals. Co-stimulatory signals can amplify the magnitude of the primary signals and suppress cell death following initial stimulation resulting in a more durable activation state and thus a higher cytotoxic capacity. A "co-stimulatory signal" refers to a signal, which in combination with a primary signal, such as TCR/CD3 ligation, leads to T cell and/or NK cell proliferation and/or upregulation or downregulation of key molecules.

"Anti-idiotype antibody" or "anti-idiotypic antibody" refers to an antibody that specifically binds to the variable region of another antibody. In the case of KLK2, an anti-idiotype antibody specifically binds an anti-KLK2 antibody.

"Antigen-binding portion," "antigen-binding fragment" or "antigen-binding domain" refers to a portion of the protein that binds an antigen. Antigen binding portions may be synthetic, enzymatically obtainable or genetically engineered polypeptides and include portions of an immunoglobulin that bind an antigen, such as the VH, the VL, the VH and the VL, Fab, Fab', F(ab')$_2$, Fd and Fv fragments, domain antibodies (dAb) consisting of one VH domain or one VL domain, shark variable IgNAR domains, camelized VH domains, VHH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3, alternative scaffolds that bind an antigen, and multi specific proteins comprising the antigen binding portions. Antigen binding portions (such as VH and VL) may be linked together via a synthetic linker to form various types of single antibody designs where the VH/VL domains may pair intramolecularly, or intermolecularly in those cases when the VH and VL domains are expressed by separate single chains, to form a monovalent antigen binding domain, such as single chain Fv (scFv) or diabody. Antigen binding portions may also be conjugated to other antibodies, proteins, antigen binding portions or alternative scaffolds which may be monospecific or multispecific to engineer bispecific and multispecific proteins.

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antigen binding sites in an antibody. CDRs may be defined using various terms: (i) Complementarity Determining Regions (CDRs), three in the VH (HCDR1, HCDR2, HCDR3) and three in the VL (LCDR1, LCDR2, LCDR3) are based on sequence variability (Wu and Kabat, J Exp Med 132:211-50, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3) refer to the regions of an antibody variable domains which are hypervariable in structure as defined by Chothia and Lesk (Chothia and Lesk, Mol Biol 196:901-17, 1987). The International ImMunoGeneTics (IMGT) database (http://www_imgt_org) provides a standardized numbering and definition of antigen-binding sites. The correspondence between CDRs, HVs and IMGT delineations is described in Lefranc et al., Dev Comparat Immunol 27:55-77, 2003. The term "CDR", "HCDR1", "HCDR2", "HCDR3", "LCDR1", "LCDR2" and "LCDR3" as used herein includes CDRs defined by any of the methods described supra, Kabat, Chothia or IMGT, unless otherwise explicitly stated in the specification.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Modulate" refers to either enhanced or decreased ability of a test molecule to mediate an enhanced or a reduced response (i.e., downstream effect) when compared to the response mediated by a control or a vehicle.

"Natural killer cell" and "NK cell" are used interchangeably and synonymously herein. NK cell refers to a differentiated lymphocyte with a $CD16^+$ $CD56^+$ and/or $CD57^+$ $TCR^-$ phenotype. NK cells are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"Specifically binds," "specific binding," "specifically binding" or "binds" refer to a proteinaceous molecule binding to an antigen or an epitope within the antigen with greater affinity than for other antigens. Typically, the proteinaceous molecule binds to the antigen or the epitope within the antigen with an equilibrium dissociation constant ($K_D$) of about $1 \times 10^{-7}$ M or less, for example about $5 \times 10^{-8}$ M or less, about $1 \times 10^{-8}$ M or less, about $1 \times 10^{-9}$ M or less, about $1 \times 10^{-10}$ M or less, about $1 \times 10^{-11}$ M or less, or about $1 \times 10^{-12}$ M, $1 \times 10^{-13}$ M, $1 \times 10^{-14}$ M, $1 \times 10^{-15}$ M or less, typically with the $K_D$ that is at least one hundred fold less than its $K_D$ for binding to a non-specific antigen (e.g., BSA, casein). In the context of the prostate neoantigens described here, "specific binding" refers to binding of the proteinaceous molecule to the prostate neoantigen without detectable binding to a wild-type protein the neoantigen is a variant of.

"Tumor cell" or a "cancer cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo.

The term "chimeric antigen receptor" or "CAR" as used herein is defined as a cell-surface receptor comprising an extracellular target-binding domain, a transmembrane domain and an intracellular signaling domain, all in a combination that is not naturally found together on a single protein. This particularly includes receptors wherein the extracellular domain and the intracellular signaling domain are not naturally found together on a single receptor protein. The chimeric antigen receptors of the present invention are intended primarily for use with lymphocyte such as T cells and natural killer (NK) cells.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs", which refer to T cells that suppress an abnormal or excessive immune response and play a role in immune tolerance. Tregs are typically transcription factor Foxp3-positive CD4+ T cells and can also include transcription factor Foxp3-negative regulatory T cells that are IL-10-producing CD4+ T cells.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotype (anti-Id) antibodies (including, e.g., anti-Id antibodies to antigen-specific TCR), and epitope-binding portions of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5a, JM109, and KCB, SURE® Competent Cells, and SOLO-PACK Gold Cells, can be used as host cells for vector replication and/or expression. Additionally, bacterial cells such as E. coli LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid; these terms may also refer to the nucleic acid sequence including the portion coding for any amino acids added as an artifact of cloning, including any amino acids coded for by linkers.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

"Kallikrein related peptidase 2", "hK2" "KLK2", or "klk2" refers to a known protein which is also called kallikrein-2, glandular kallikrein 2, or HK2. hK2 is produced as a preproprotein and cleaved during proteolysis to generate active protease. All hK2 isoforms and variants are encompassed in "hK2". The amino acid sequences of the various isoforms are retrievable from GenBank accession numbers NP_005542.1, NP_001002231.1 and NP_001243009. The amino acid sequence of a full length hK2 is shown in SEQ ID NO:47. The sequence includes the signal peptide (residues 1-18) and the pro-peptide region (residues 19-24).

The term "KL2B413" refers to any antibody, antigen-binding portion thereof, or any other protein that contains variable regions derived from KL2B413 VH (SEQ ID 41) and KL2B413 VL (SEQ ID 42), including a CAR. In certain embodiments, an anti-idiotype antibody of the disclosure specifically binds a protein comprising a VH domain as set forth in SEQ ID NO: 41 and/or a VL domain as set forth in SEQ ID NO: 42. In certain embodiments, an anti-idiotype antibody of the disclosure specifically binds a protein comprising the 3 CDRs of the VH domain set forth in SEQ ID NO: 41 and the 3 CDRs of the VL domain set forth in SEQ ID NO: 42.

The term "KL2B513" refers to a KL2B413-derived scFv-Fusion protein with the variable regions in the VL-VH orientation. KL2B513 may be referred to interchangeably as KL2B413-LH-scFv.

The term "KL2B610" refers to a KL2B413-derived scFv-Fusion protein with the variable regions in the VH-VL orientation. KL2B610 may be referred to interchangeably as KL2B413-HL-scFv.

The term "A002B39" refers to a chimeric mAb with human VH/VL targeting KL2B413 and murine IgG2a/k. A002B39 may be referred to interchangeably as A002M39.

The terminology used herein is for the purpose of describing particular embodiments only and is not intended to be limiting. As used herein, the indefinite articles "a", "an" and "the" should be understood to include plural reference unless the context clearly indicates otherwise.

The disclosure further provides variants, e.g., functional variants, of the antibodies, nucleic acids, polypeptides, and proteins described herein. "Variant" refers to a polypeptide or a polynucleotide that differs from a reference polypeptide or a reference polynucleotide by one or more modifications for example, substitutions, insertions or deletions. The term "functional variant" as used herein refers to an antibody polypeptide, or protein having substantial or significant sequence identity or similarity to a parent antibody, polypeptide, or protein, which functional variant retains the biological activity of the antibody, polypeptide, or protein for which it is a variant. Functional variants encompass, e.g., those variants of the antibody, polypeptide, or protein described herein (the parent antibody, polypeptide, or protein) that retain the ability to recognize target cells to a similar extent, the same extent, or to a higher extent, as the parent antibody, polypeptide, or protein. In reference to the parent antibody, polypeptide, or protein, the functional variant can, for example, be at least about 30%, about 40%, about 50%, about 60%, about 75%, about 80%, about 85%, about 90%, about 91%, about 92%, about 93%, about 94%, about 95%, about 96%, about 97%, about 98%, about 99% or more identical in amino acid sequence to the parent antibody, polypeptide, or protein.

Herein, the structure of polypeptides is in places defined on the basis of % sequence identity with a recited reference sequence (with a given SEQ ID NO). In this context, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. Typically, the comparison window with correspond to the full length of the sequence being compared. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program. Determining sequence identity of a query sequence to a reference sequence is within the ability of the skilled person and can be performed using commercially available analysis software such as BLAST'.

A functional variant can, for example, comprise the amino acid sequence of the parent antibody, polypeptide, or protein with at least one conservative amino acid substitution. In another embodiment, the functional variants can comprise the amino acid sequence of the parent antibody, polypeptide, or protein with at least one non-conservative amino acid substitution. In this case, the non-conservative amino acid substitution may not interfere with or inhibit the biological activity of the functional variant. The non-conservative amino acid substitution may enhance the biological activity of the functional variant such that the biological activity of the functional variant is increased as compared to the parent antibody, polypeptide, or protein.

Amino acid substitutions of the inventive antibodies may be conservative amino acid substitutions. Conservative amino acid substitutions are known in the art, and include amino acid substitutions in which one amino acid having certain physical and/or chemical properties is exchanged for another amino acid that has the same or similar chemical or physical properties. For example, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The antibodies, polypeptides, and proteins of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, α-(2-amino-2-norbornane)-carboxylic acid, α,γ-diaminobutyric acid, α,β-diaminopropionic acid, homophenylalanine, 4-chlorophenylalanine, 4-carboxyphenylalanine, β-phenyl serine β-hydroxyphenylalanine, phenylglycine, α-naphthylalanine, cyclohexylalanine, cyclohexylglycine, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, indoline-2-carboxylic acid, 1,2,3,4-tetrahydroisoquinoline-3-carboxylic acid, aminomalonic acid, aminomalonic acid monoamide, and α-tert-butylglycine.

The antibodies, polypeptides, and proteins of embodiments of the invention (including functional portions and functional variants) can be subject to post-translational modifications. They can be glycosylated, esterified, N-acylated, amidated, carboxylated, phosphorylated, esterified, cyclized via, e.g., a disulfide bridge, or converted into an acid addition salt. In some embodiments, they are dimerized or polymerized, or conjugated.

The antibodies, polypeptides, and/or proteins of embodiments of the invention (including functional portions and functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; and Epitope Mapping, ed. Westwood et al., Oxford University Press, Oxford, United Kingdom, 2001. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994. Further, some of the antibodies, polypeptides, and proteins of the invention (including functional portions and functional variants thereof) can be isolated and/or purified from a source, such as a plant, a bacterium, an insect, a mammal, etc. Methods of isolation and purification are known in the art. Alternatively, the antibodies, polypeptides, and/or proteins described herein (including functional portions and functional variants thereof) can be commercially synthesized. In this respect, the antibodies, polypeptides, and proteins can be synthetic, recombinant, isolated, and/or purified.

Methods and Uses of the Disclosure

The disclosure provides anti-idiotype antibodies and antigen-binding portions thereof that specifically bind a KL2B413 containing protein, e.g., an antibody or antigen-binding portions thereof. For example, the anti-idiotype antibodies may include amino acid sequences complementary to portions of a KL2B413 antibody to facilitate specific binding. The disclosure also provides nucleic acids encoding the anti-idiotype antibodies and antigen-binding portions thereof, methods of producing the anti-idiotype antibodies and antigen-binding portions thereof, methods of detecting KL2B413 using the anti-idiotype antibodies and antigen-binding portions thereof and kits including the anti-idiotype antibodies and antigen-binding portions thereof. For example, the anti-idiotype antibodies may be included in kits containing other reagents and used to determine whether a given biological sample includes KL2B413 antibodies or fragments thereof, for example, expressed on the surface of a T cell in a CAR.

Methods of testing antibodies for the ability to bind to any functional portion of KL2B413 are known in the art and include any antibody-antigen binding assay, such as, for example, radioimmunoassay (RIA), Western blot, enzyme-linked immunosorbent assay (ELISA), immunoprecipitation, and competitive inhibition assays.

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display can also be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

In one aspect, the disclosure provides an anti-idiotype antibody or antigen-binding portion thereof that specifically binds a target antibody or CAR that comprises KL2B413. For example, the anti-idiotype antibody or antigen-binding portion may specifically bind one or more of the domains of the fragment antigen-binding region (Fab), including the VH and VL. In some embodiments, the anti-idiotype antibody or antigen-binding portion comprises a VH domain with an amino acid sequence of SEQ ID NOs:45 and a VL domain with an amino acid sequence of SEQ ID NOs:46.

In other embodiments, the anti-idiotype antibody or antigen-binding portion is for use in detecting KL2B413 in a biologic sample comprising: (a) providing a biological sample; (b) contacting the biological sample with the anti-idiotype antibody or antigen-binding portion; and (c) detecting the anti-idiotype antibody or antigen-binding portion. For example, an anti-idiotype antibody may be added to any biologic sample, including: a tissue sample, a tumor sample, a cell or a fluid with other biological components, organisms, subunits of proteins/antigens, killed or inactivated whole cells or lysates. The anti-idiotype antibody may be contained in a solution containing pharmaceutically acceptable reagents, including but not limited to buffers, a stabilizer, and/or polymers. The anti-idiotype antibody may be contacted by pipetting and/or mixing with the biologic sample. Then anti-idiotype antibody may then specifically bind a KL2B413 containing protein, e.g., an antibody or antigen-binding portions thereof, in the biologic sample. As one example, whether an anti-idiotype antibody has bound to KL2B413 may be determined by washing unbound anti-idiotype antibody, leaving only complexed anti-idiotype antibody. Continuing with this example, the anti-idiotype antibody may include a fluorophore, which may be illuminated to give a signal proportional to the amount of KL2B413 in the biologic sample. Detection of a bound complex of anti-idiotype antibody to KL2B413 is described further below.

In another aspect, the disclosure provides an anti-idiotype antibody or antigen-binding portion that specifically binds an anti-KLK2 antibody that comprises a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprises a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NOs:33-34. The six CDRs may be selected according to any known methods. The VH and VL CDRs determined according to Kabat, AbM, Chothia and contact methods are shown in Table 3.

In certain embodiments, the disclosure provides an anti-idiotype antibody or antigen-binding portion that specifically binds an anti-KLK2 antibody that comprises a heavy chain variable (VH) domain comprising a VH CDR1 having an amino acid sequence of SEQ ID NO:4, a VH CDR2 having an amino acid sequence of SEQ ID NO:11 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-KLK2 antibody that comprises a heavy chain variable (VH) domain comprising a VH CDR1 having an amino acid sequence of SEQ ID NO:5, a VH CDR2 having an amino acid sequence of SEQ ID NO:12 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-KLK2 antibody that comprises a heavy chain variable (VH) domain comprising a VH CDR1 having an amino acid sequence of SEQ ID NO:6, a VH CDR2 having an amino acid sequence of SEQ ID NO:13 and a VH CDR3 having an amino acid sequence of SEQ ID NO:19, and further comprises a light chain variable (VL) domain comprising a VL CDR1 having an amino acid sequence of SEQ ID NO:25, a VL CDR2 having an amino acid sequence of SEQ ID NO:29 and a VL CDR3 having an amino acid sequence of SEQ ID NO:33.

In certain embodiments, the disclosure provides an anti-idiotype antibody or antigen-binding portion that specifically binds an anti-KLK2 antibody that comprises a heavy chain variable (VH) domain comprising a VH CDR1 having an amino acid sequence of SEQ ID NO:7, a VH CDR2 having an amino acid sequence of SEQ ID NO:14 and a VH CDR3 having an amino acid sequence of SEQ ID NO:20, and further comprises a light chain variable (VL) domain comprising a VL CDR1 having an amino acid sequence of SEQ ID NO:26, a VL CDR2 having an amino acid sequence of SEQ ID NO:30 and a VL CDR3 having an amino acid sequence of SEQ ID NO:34.

In some embodiments, the anti-idiotype antibody or antigen-binding portion thereof that specifically binds an anti-KLK2 antibody comprises a VH domain that has an amino acid sequence having at least 90% sequence identity to SEQ ID NO:45 and the VL domain has an amino acid sequence having at least 90% sequence identity to SEQ ID NO:46. In some embodiments, the anti-idiotype antibody or antigen-binding portion thereof that specifically binds an anti-KLK2 antibody comprises a heavy chain comprising an amino acid sequence having at least 90% sequence identity to SEQ ID NO: 37 and further comprises a light chain comprising an amino acid sequence having at least 90% sequence identity to SEQ ID NO:39.

In some embodiments, the anti-idiotype antibody or antigen-binding portion thereof that specifically binds an anti-KLK2 antibody comprises a VH domain that has an amino acid sequence of SEQ ID NO:45 and a VL domain that has an amino acid sequence of SEQ ID NO:46. In some other embodiments, the anti-idiotype antibody or antigen-binding portion thereof that specifically binds an anti-KLK2 antibody comprises a heavy chain comprising an amino acid sequence of SEQ ID NO:37 and further comprises a light chain comprising an amino acid sequence of SEQ ID NO:39.

In some embodiments, the antigen-binding portion is selected from a Fab, F(ab')$_2$, or scFv. In some embodiments, the antibody is a monoclonal antibody. In some embodiments, the antibody is a chimeric antibody. In some embodiments, the chimeric antibody comprises a murine IgG2a framework. In certain embodiments, the murine IgG2a framework may include a murine Ig heavy chain signal peptide from mix FVB/N, C57BL/6J comprising the sequence MAWVWTLLFLMAAAQSIQA (SEQ ID NO: 48).

In some other embodiments, the antibody is a fully human antibody. For example, the fully human antibody may be an IgG, IgM, IgA, IgE, or IgD. In some embodiments, the anti-idiotype antibody or antigen-binding portion thereof is specific to KL2B413, wherein KL2B413 is within the antigen-binding domain of the extracellular portion of a chimeric antigen receptor (CAR). For example, a KL2B413 encoding nucleic acid may be introduced in vitro into a T-cell, of which at least some portion then is expressed on the extracellular portion of a CAR. The anti-idiotype antibody may then specifically bind the extracellular portion of the CAR. In some embodiments, KL2B413 is an scFv and the anti-idiotype antibody or antigen-binding portion specifically binds an epitope in the scFv of the CAR. In some embodiments, KL2B413 specifically binds KLK2. In some embodiments, the antibody or antigen-binding portion does not cross-react to other KLK2 antibodies or other KLK2 binding CARs. For example, to prevent false positives in an assay for determining whether KL2B413 has been expressed on the extracellular portion of a CAR, the anti-idiotype antibody may be specific to KL2B413, and not have appreciable binding to its target KLK2 or other KLK2 targeting ligands that are not KL2B413. In some embodiments, the CAR has an amino acid sequence selected from the group consisting of SEQ ID NOs.:43-44.

In some embodiments, the disclosure provides a nucleic acid encoding the heavy chain, the light chain, or both, of the anti-idiotype antibody or antigen-binding portion. For example, the nucleic acid may be DNA, RNA, and any chemical modifications thereto (e.g., nucleoside modifications).

In another aspect, the disclosure provides a nucleic acid encoding the heavy chain, the light chain, or both, of an anti-idiotype antibody or an antigen-binding portion thereof that specifically binds KL2B413, wherein said nucleic acid comprises: the nucleotide sequence of SEQ ID NO: 38; the nucleotide sequence of SEQ ID NO: 40; or both. In another aspect, the disclosure provides a vector comprising the nucleic acid sequence. For example, the vector may be a self-replicating nucleic acid structure, or incorporated into the genome of a host cell into which it has been introduced. In some embodiments, the vector is an expression vector. In another aspect, the disclosure provides a host cell comprising the vector. In some embodiments, the host cell is a mammalian cell.

In another aspect, the disclosure provides a method of producing an anti-idiotype antibody or antigen-binding portion thereof that specifically binds KL2B413, said method comprising culturing a host cell under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture. For example, the anti-idiotype antibody may be produced by homogenous suspension culture in deep-tank stirred fermenters, perfusion-tank systems, airlift reactors, and continuous-culture systems. Anti-idiotype antibodies may be isolated from reaction and/or growth mixtures by physical or chemical separation procedures, including affinity separation using Protein A or G, size exclusion chromatography, and charge separations. In some embodiments, the host cell encodes a vector comprising a nucleic acid encoding the anti-idiotype antibody or antigen-binding portion thereof.

In another aspect, the disclosure provides a method for detecting KL2B413 in a biologic sample comprising: (a) providing a biological sample; (b) contacting the biological sample with the anti-idiotype antibody or antigen-binding portion; and (c) detecting the anti-idiotype antibody or antigen-binding portion. For example, the anti-idiotype antibody may bind KL2B413 expressed in the biological sample. The bound complex may be detected by any detection method, including both chemical and physical detection methods. For example, the detecting method may be used to identify the mere presence of the antibody of interest in a biological sample, or may be used to test whether the antibody of interest in a sample is present at a detectable level, or may be used to quantify the amount of the antibody of interest in a sample and further to compare the antibody levels from different samples. For example, the detecting method may be one or more of: immunoprecipitation, immunocytochemistry, immunoblotting, and immunosorbent assays. As a specific example, the immunsorbent assay may be an ELISA or ELISA-type assay that includes a bound anti-idiotype antibody or fragment thereof over which the biologic sample is washed.

In another aspect, the disclosure provides a method for detecting expression of a chimeric antigen receptor (CAR) comprising KL2B413 in a biologic sample comprising: (a) providing a biological sample; (b) contacting the biological sample with the anti-idiotype antibody or antigen-binding portion; and (c) detecting the anti-idiotype antibody or antigen-binding portion, and thereby detecting the expression of the CAR.

In some embodiments, the antibody comprises a detectable label. In some embodiments, the method further comprises further comprises contacting the anti-idiotype antibody or antigen-binding portion with a detectable label before detecting the anti-idiotype antibody or antigen-binding portion. For example, the detectable label may be any chemical tag or component that is either integral to, binds to, or otherwise complexes to the anti-idiotype antibody and emits or otherwise provides a unique identifiable signal. For example, the detectable label may be an isotope marker, colorimetric biosensor, photochromic compound, fluorescent label, fluorogenic label, or electrochemical sensor. As a specific example, the fluorescent label may be green fluorescent protein, yellow fluorescent protein, blue fluorescent protein, fluorescein, rhodamine, coumarin, cyanine, phycoerythrin, and derivatives thereof.

In some embodiments, the biological sample is blood, serum or urine. For example, the biological sample may be whole blood, serum, plasma, urine, feces, cerebrospinal fluid, ascites, and the like. In some embodiments, the biological sample is fresh biological material, such as biological material taken at a given time for the purpose of this analysis. The biological sample may also be biological material taken at another point during patient care for this or for other purposes, or using archived patient material. The biological sample may be freshly obtained or previously obtained, and where previously obtained may have been stored prior to use (e.g., at room temperature, refrigerated, or frozen).

In some aspects, the disclosure provides a kit for detecting KL2B413 in a biologic sample comprising: (a) an anti-idiotype antibody or antigen-binding portion; and (b) instructions for detecting the anti-idiotype antibody or antigen-binding portion. For example, the kit may include the anti-idiotype antibody or antigen-binding portion as a solid powder, lyophilized powder, liquid solution or liquid components to mix to form a solution, or bound to a solid support. The kit may include additional reagents, including stabilizers, buffers, and other pharmaceutically acceptable excipients needed to facilitate using the kit in an assay of a biological sample. The kit may also include written instructions directing a user on how to perform the assay.

In other aspects, the disclosure provides a method of purifying KL2B413 from a sample comprising: (a) providing a biological sample comprising KL2B413; (b) contacting the biological sample with an anti-idiotype antibody or antigen-binding portion of the disclosure; and (c) capturing the anti-idiotype antibody or antigen-binding portion, including a CAR or other protein that contains KL2B413, and thereby purifying KL2B413. For example, any separation method, including physical and chemical methods, may be used to capture the anti-idiotype antibody. Specifically, the KL2B413 can be captured and isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the anti-idiotype antibody. In some embodiments, the anti-idiotype antibody is a fusion protein containing a domain which facilitates its purification. In certain embodiments, a purified KL2B413 composition is substantially isolated from proteins that do not contain KL2B413. In some embodiments, a purified KL2B413 composition is 100% pure, 99% pure, 98% pure, 97% pure, 96% pure, 95% pure, or 90% pure or greater.

In other aspects, the disclosure provides a method of selecting CAR-T cells from a cell population comprising: (a) providing a biological sample comprising CAR-T cells; (b) contacting the biological sample with an anti-idiotype antibody or antigen-binding portion; and (c) capturing the anti-idiotype antibody or antigen-binding portion, and thereby selecting CAR-T cells. In some embodiments, the anti-idiotype antibody or antigen-binding portion thereof is specific to KL2B413.

EMBODIMENTS

Particular non-limiting embodiments of the invention are set forth in the following numbered paragraphs.

1. An anti-idiotype antibody or antigen-binding portion thereof that specifically binds a target antibody that comprises KL2B413.

2. The anti-idiotype antibody or antigen-binding portion of paragraph 1, wherein the target antibody or antigen-binding portion thereof comprises a VH domain with an amino acid sequence of SEQ ID NO:41 and a VL domain with an amino acid sequence of SEQ ID NO: 42.

3. An anti-idiotype antibody or an antigen-binding portion thereof that specifically binds KL2B413, wherein the anti-idiotype antibody or antigen-binding portion comprises a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprises a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34.

4. The anti-idiotype antibody or antigen-binding portion of any one of paragraphs 1-3, wherein the VH domain has an amino acid sequence having at least 90% sequence identity to SEQ ID NO:45 and the VL domain has an amino acid sequence having at least 90% sequence identity to SEQ ID NO:46.

5. The anti-idiotype antibody or antigen-binding portion of any one of paragraphs 1-3, wherein the anti-idiotype antibody or antigen-binding portion comprises a heavy chain comprising an amino acid sequence having at least 90% sequence identity to SEQ ID NO:37 and further comprises a light chain comprising an amino acid sequence having at least 90% sequence identity to SEQ ID NO:39.

6. The anti-idiotype antibody or antigen-binding portion of any one of paragraphs 1-3, wherein the VH domain has an amino acid sequence of SEQ ID NO:45 and the VL domain has an amino acid sequence of SEQ ID NO:46.

7. The anti-idiotype antibody or antigen-binding portion of any one of paragraphs 1-3, wherein the anti-idiotype antibody or antigen-binding portion comprises a heavy chain comprising an amino acid sequence of SEQ ID NO:37 and further comprises a light chain comprising an amino acid sequence of SEQ ID NO:39.

8. The anti-idiotype antibody or antigen-binding portion of any one of paragraphs 1-3, wherein the antigen-binding portion is selected from a Fab, F(ab')$_2$, or scFv.

9. The anti-idiotype antibody or antigen-binding portion of any one of paragraphs 1-3, wherein the antibody is a monoclonal antibody.

10. The anti-idiotype antibody or antigen-binding portion of any one of paragraphs 1-3, wherein the antibody is a chimeric antibody.

11. The anti-idiotype antibody or antigen-binding portion of paragraph 10, wherein the antibody comprises a murine IgG2a framework.

12. The anti-idiotype antibody or antigen-binding portion of any one of paragraphs 1-3, wherein the antibody is a fully human antibody.

13. A nucleic acid encoding the heavy chain, the light chain, or both, of the anti-idiotype antibody or antigen-binding portion of any one of paragraphs 1-3.

14. A nucleic acid encoding the heavy chain, the light chain, or both, of an anti-idiotype antibody or an antigen-binding portion thereof that specifically binds KL2B413, wherein said nucleic acid comprises:
   a) the nucleotide sequence of SEQ ID NO: 38;
   b) the nucleotide sequence of SEQ ID NO: 40;
   c) both a) and b).

15. A vector comprising the nucleic acid of paragraph 14.

16. The vector of paragraph 15, wherein the vector is an expression vector.

17. A host cell comprising the vector of paragraph 16.

18. The host cell of paragraph 17, wherein the cell is a mammalian cell.

19. A method of producing an anti-idiotype antibody or antigen-binding portion thereof that specifically binds KL2B413, said method comprising culturing the host cell of paragraph 17 under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture.

20. A method for detecting KL2B413 in a biologic sample comprising: (a) providing a biological sample; (b) contacting the biological sample with the anti-idiotype antibody or antigen-binding portion of any one of paragraphs 1-3; and (c) detecting the anti-idiotype antibody or antigen-binding portion.

21. A method for detecting expression of a chimeric antigen receptor (CAR) comprising KL2B413 in a biologic sample comprising: (a) providing a biological sample; (b) contacting the biological sample with the anti-idiotype antibody or antigen-binding portion of any one of paragraphs 1-3; and (c) detecting the anti-idiotype antibody or antigen-binding portion, and thereby detecting the expression of the CAR.

22. The method according to paragraph 20, wherein the antibody comprises a detectable label.

23. The method according to paragraph 20, wherein the method further comprises contacting the anti-idiotype antibody or antigen-binding portion with a detectable label before detecting the anti-idiotype antibody or antigen-binding portion.

24. The method according to paragraph 20, wherein the biological sample is blood, serum or urine.

25. The anti-idiotype antibody or antigen-binding portion of any one of paragraphs 1-3, wherein KL2B413 is within the antigen-binding domain of the extracellular portion of a chimeric antigen receptor (CAR).

26. The anti-idiotype antibody or antigen-binding portion of paragraph 25 wherein KL2B413 is an scFv and the anti-idiotype antibody or antigen-binding portion specifically binds an epitope in the scFv of the CAR.

27. The anti-idiotype antibody or antigen-binding portion of paragraph 25, wherein KL2B413 binds KLK2.

28. The anti-idiotype antibody or antigen-binding portion of paragraph 25, wherein the antibody or antigen-binding portion does not cross-react to other KLK2 antibodies or other KLK2 binding CARs.

29. The anti-idiotype antibody or antigen-binding portion of paragraph 25, wherein the CAR has an amino acid sequence selected from the group consisting of SEQ ID NOs: 43-44.

30. A kit for detecting KL2B413 in a biologic sample comprising: (a) the anti-idiotype antibody or antigen-binding portion of any one of paragraphs 1-3; and (b) instructions for detecting the anti-idiotype antibody or antigen-binding portion.

31. The anti-idiotype antibody or antigen-binding portion of any one of paragraphs 1-3, for use in detecting KL2B413 in a biologic sample comprising: (a) providing a biological sample; (b) contacting the biological sample with the anti-idiotype antibody or antigen-binding portion; and (c) detecting the anti-idiotype antibody or antigen-binding portion.

32. A method of purifying KL2B413 from a sample comprising: (a) providing a biological sample comprising KL2B413; (b) contacting the biological sample with the anti-idiotype antibody or antigen-binding portion of any one of paragraphs 1-3; and (c) capturing the anti-idiotype antibody or antigen-binding portion, and thereby purifying KL2B413.

33. A method of selecting CAR-T cells from a cell population comprising: (a) providing a biological sample comprising CAR-T cells; (b) contacting the biological sample with the anti-idiotype antibody or antigen-binding portion of any one of paragraphs 1-3; and (c) capturing the anti-idiotype antibody or antigen-binding portion, and thereby selecting CAR-T cells.

EXAMPLES

Example 1: Determination of KL2B513 or KL2B610 Binding Fabs

KL2B413-derived scFv-Fusion protein binding Fabs were selected from two sets of de novo Fab-pIX phage display libraries as described in Shi et al., J Mol Biol 397:385-96, 2010; Int. Pat. Publ. No. WO2009/085462; U.S. Pat. Publ. No. US2010/0021477). There are two KL2B413-derived scFv-Fusion proteins: KL2B513 (VL-VH) and KL2B610 (VH-VL), with difference in the orientation of VH and VL within scFv.

In the phage selections using purified recombinant antigens, biotinylated KL2B513 or KL2B610 were used as "bait" to capture and immobilize the phage binders. After several selection rounds, a polyclonal phage ELISA using purified antigens was performed to detect the specific enrichment of individual panning experiments. The phage collected from those panning experiments which demonstrated enrichment for binders to KL2B513 or KL2B610 were expressed in *E. coli* for primary screening. Monoclonal Fab lysates were prepared from the enriched Fab libraries were screened in ELISA for binding to KL2B513 or KL2B610 but not to a similar negative control scFv fusion protein GC5B734 or GCDB332. The selected Fabs were sequenced to identify the unique Fab clones and isolate their V region genes. The unique Fab V regions were cloned into mammalian expression vectors to express chimeric mAbs with murine IgG2a/murine Kappa constant regions. The chimeric mAbs were evaluated for specific binding to the KL2B413-derived scFv expressed on SupT1 cells which corresponds to the scFv in the KL2B513 or KL2B610 scFv fusion protein, and binding kinetics were measured using SPR.

Phage Panning

Six individual panning experiments using individual V3.0 and V5.0 de novo Fab phage libraries were panned against biotinylated KL2B513 or KL2B610 according to standard protocol (Cheadle, E. J. et al. Antibody Engineering. 907, 645-666 (2012). Briefly, the phage libraries and paramagnetic streptavidin (SA) beads were blocked in 50% Chemiblocker (Millipore cat #2170)/50% 1×TBST (Teknova cat #T0310) for one hour. Libraries were added to the SA beads to adsorb clones that bind non-specifically to the beads. SA-beads were discarded, and the pre-adsorbed library was added to biotinylated KL2B513 or KL2B610 with the presence of 100 nM of GP5B305. Binders were retrieved by addition of SA-beads to form a bead/antigen/phage complex, which was washed in 1×TBST. After the final wash, phage was rescued by infection of log phase TG1 E. coli cells (OD600 nm=0.4-0.6). The phage-infected TG1 cells was spread on three 150-mm LB/Agar plates containing 75 µg/ml carbenicillin and 1% glucose then grown overnight at 37° C. Phage was produced and subjected for additional panning. To increase selection pressure, the antigen concentration was reduced at room temperature for each subsequent rounds: R1 100 nM, 1 hour; R2 50 nM 1 hour; R3 10 nM 1 hour, R4 5 nM 1 hour.

Polyclonal Phage ELISA

Enrichment of binders was determined from each panning experiment by polyclonal phage ELISA. Briefly, 100 µl of 20 nM nonbiotinylated KL2B513 or KL2B610 diluted in 1×TBS (Teknova cat #T9530) was captured on NA-coated plate (Thermo cat #15217). After an hour incubation at 37° C., the plate was washed 3 times in 300l_11 1×TBST. 300 µl of blocking buffer 50% Chemiblocker/50% 1×TBST was added to each well of the plate and incubated at room temperature for 1 hour. After blocking, the plate was washed 3 times with 300l_11 of 1×TBST. 100l, of polyclonal phage output from each panning rounds diluted 1/100 diluted in assay buffer, 10% Chemiblocker/90% TBST, were added to the ELISA plate and incubated at room temperature for 1 hour to allow the binding of Fab displayed on the phage particles to the immobilized KL2B513 or KL2B610. Following the incubation, the plate was washed 3 times with 1×TBST. 100 µl of HRP-conjugated anti-M13 (pVIII) antibody (GE Healthcare cat #27942101) diluted 1:2500 in assay buffer was added to the plate and incubated at room temperature. After 1 hour incubation, the plate was washed 6 times with 300l_11 of 1×TBST. 100 µL of prepared BM chemiluminescence ELISA Substrate (Roche cat #11582950001) was added to the plate. The chemiluminescence or relative light unit (RLU) was measured by Envision plate reader.

FIG. 1 shows the results of the polyclonal phage ELISA. Round 1 to round 4 panning outputs from 12 panning experiments were screened on NA-coated plates in binding to KL2B513 or KL2B610, and negative control GCDB332. Panning outputs with specific enrichment were selected for monoclonal Fab production. A002B39 was derived from APD316XP_19 panning experiment.

Fab Production

Plasmid DNA were isolated and purified from glycerol stocks of specific rounds of phage panning experiments that were identified to demonstrate enrichment of binders to KL2B513 or KL2B610, and transformed into TG-1 E. coli cells and grown on LB/Agar plates overnight. The overnight cultures were used for (i) colony PCR and sequencing of the V regions, and (ii) starting culture for Fab production. For Fab production, the overnight culture was diluted 10-100 fold in new media and grown for 5-6 hours at 37° C. Fab production was induced by the addition of fresh media containing IPTG and the cultures were grown overnight at 30° C. The cultures were spun down and the bacterial pellet was lysed using BugBuster™ (Millipore) to release the soluble Fab proteins. The cell lysate was spun down and the supernatant were used for Fab ELISA.

Primary Screening

The phage collected from the panning experiments which demonstrated enrichment for binders to KL2B513 or KL2B610 were expressed in E. coli for primary screening. MSD 384-well streptavidin plates (Meso Scale #L21SA-5) were blocked with 50 ul/well SuperBlock T20 (TBS) Blocking Buffer (Thermo #37536) for 30 min at room temperature and then aspirated. 2.5 nM biotinylated ScFv-Fc fusion antigens, target antigen KL2B513 or KL2B610, or counter screening reagent GCDB734, were added to the blocked 384-well MSD plates and incubated on a shaker for 30 min at room temperature. The plates were washed twice with 80 ul/well with 1× phosphate-buffered saline with Tween detergent ("1×PBST") and crude Fab lysates from E. coli expressions in 96-well plates were stamped into the 384-well assay plates in duplicate and incubated on a shaker for 1 h at room temperature. The assay plates were washed once with 80 ul/well of 1×PBST then 6 nM of SULFO-TAG Anti-human/NHP Kappa Antibody (Meso Scale #D20TF-6) were added at 20 ul/well and the plates incubated on a shaker for 1 h at RT. The plates were washed once with 80 ul/well 1×PBST then 35 ul/well of 1×MSD Read Buffer T (Meso Scale #R92TC-1) was added to each well and the plates analyzed on an MSD Sector 5600 plate reader. All liquid handling was performed on an Agilent Bravo system and washing of 384-well plates were handled on a BioTek 405 Select plate washer.

Figure 2:
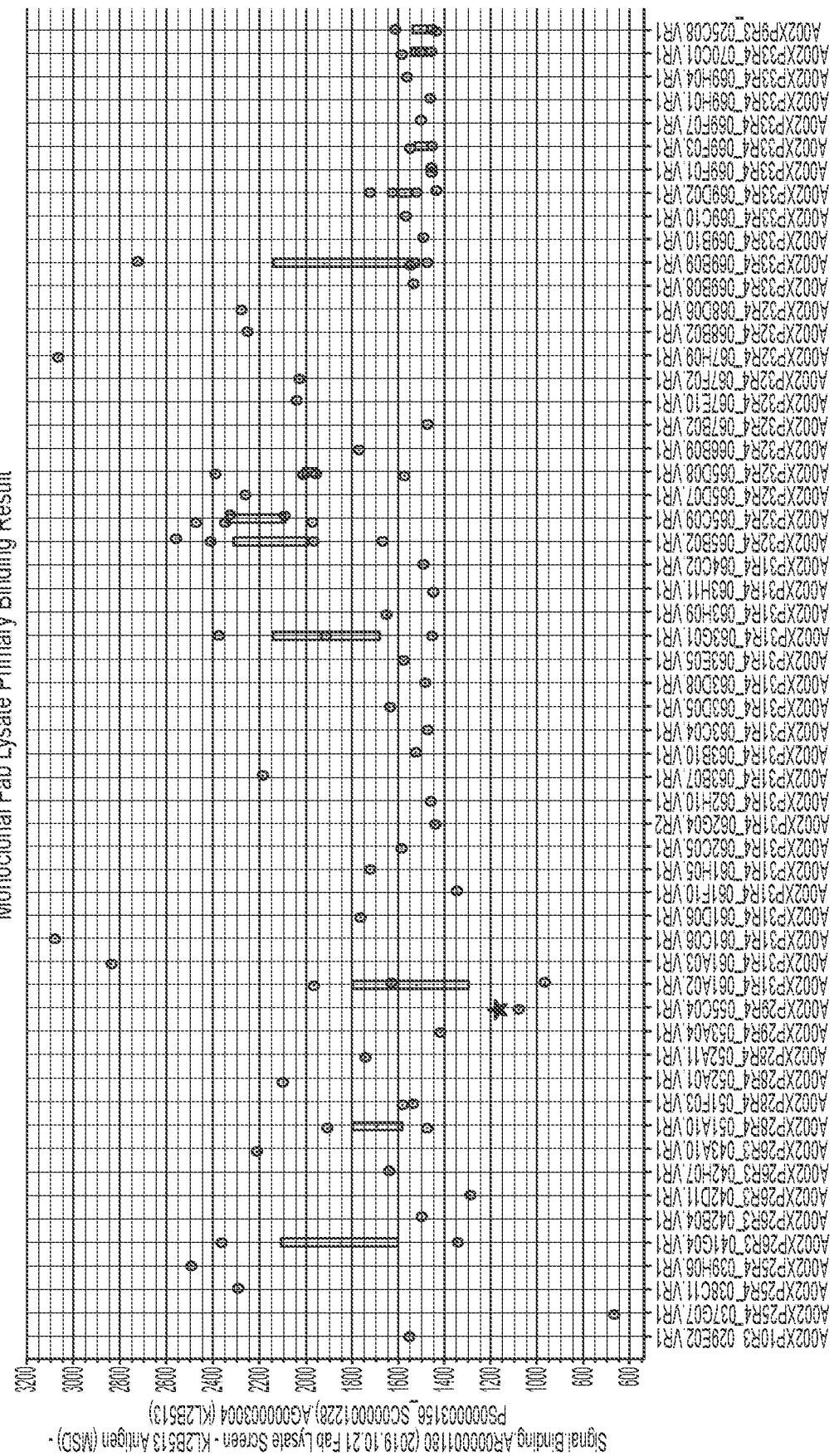
FIG. 2 shows a graphical representation of the results of monoclonal Fab binding screening from KL2B513 or KL2B610 target binding assays compared with GCDB734 counter screening reagent binding assays.

FIG. 2 shows the results of the primary screening. Monoclonal Fabs were screened on MSD plates in binding to KL2B513 or KL2B610. Clones having signal greater than the average background signal plus 3 times standard deviation in the KL2B513 or KL2B610 target binding assay and signal less than the average background signal plus 3 times standard deviation in the GCDB734 counter-reagent binding assay were selected for sequencing. The clone identified by a star is the parent clone for the VH and VL in A002B39.

Example 2: Generation of Monoclonal Antibodies Against KL2B413-LH/HL-scFv (A002B39)

Fab Selection

The selected Fabs from the primary screening were sequenced to determine V region sequences and identify unique clones. The unique Fab V regions were cloned into mammalian expression vectors to express as chimeric mAbs with murine IgG2a/murine Kappa constant regions.

The variable regions of A002B39 were identified through phage display using human Fab-pIX de novo libraries to soluble scFv-Fc fusion protein KL2B513 or KL2B610. These V regions did not undergo any affinity maturation.

The DNA sequences were obtained from the de novo Fab library without any codon optimization.

Cloning of $V_H$ and $V_L$

Two pcDNA3.1 derived mammalian expression vectors (vDR000368 and vDR000961) were used to generate the single gene constructs encoding the heavy chain (HC) or light chain (LC) of the chimeric mAb. Each vector contains a human cytomegalovirus (hCMV) promoter to drive the expression of the HC and LC and both contain the ampicillin resistance gene (Amp(R)) to facilitate cloning. vDR000368 has unique HindIII and DraIII restriction enzyme sites for cloning and also a mouse IgG2a constant region; vDR000961 has unique HindIII and Tth111I restriction enzyme sites for cloning and also a mouse Kappa constant region.

A DNA fragment comprising the variable region of HC ($V_H$) or LC ($V_L$) was synthesized and ligated into HC vector vDR000368 and LC vector vDR000961. The HC synthetic fragment included a HindIII restriction enzyme site, Kozak sequence, DNA sequences encoding a signal peptide, the VH and part of the $C_{H1}$, and a DraIII cloning site. The LC synthetic fragment included a HindIII restriction enzyme site, Kozak sequence, DNA sequences encoding a signal peptide, the VL, and part of the Kappa constant region, and a Tth111I restriction cloning site. The final HC construct is PBD000105920 and the LC construct is PBD000105921. The two constructs were co-transfected in mammalian expression cell lines HEK293 Expi or CHO to make A002B39.

Protein Expression

The HC construct PBD000105920 and the LC construct PBD000105921 were sequence verified before transfection. HEK Expi293™ cells (Thermo cat #A14527) grown in Expi293™ Expression media (Thermo cat #A1435101). The cells are grown at 37° C. shaking at 125 RPM with 8% $CO_2$. The cells were transfected at $2.5 \times 10^6$ cells per ml using Expi293™ Expression Kit (Thermo cat #A14524). For each liter of cells transfected 1 mg of total DNA was diluted in 25 ml of Opti-MEM (Thermo cat #319850620) and 2.6 ml of Expi293™ reagent was diluted in 25 ml of Opti-MEM and incubated for 5 minutes at room temperature. The diluted DNA and diluted Expi293 reagent were combined and incubated for 20 minutes at room temperature. The DNA complex was then added to the cell. The cells were placed in the shaking incubator overnight. The next day after transfection, 5 ml of Enhancer 1 was diluted into 50 ml of Enhancer 2 and the total volume of the two Enhancers were added to the cells. The transfected cells were placed back into the incubator for 4 days until harvested. The cells were removed by centrifugation at 4,500 g for 35 minutes then filtered with a 0.2 μm filter prior to checking expression levels.

Expression was quantitated using an Octet instrument. Murine IgG2 (Sigma Cat #M9144) was used as the standard. Protein A biosensors were used. The samples and the standard were diluted with spent Expi293 media. The standard curve started at 100 ug/ml in a twofold dilution. The samples were diluted 1:10. The standard curve was a linear point curve. The calculations were performed by Forte Biosystems software.

Example 3: Binding Assays for Anti-Idotypic Antibody A002B39

Binding Assay Using Soluble Proteins with Biacore

Anti-Mouse Fc antibody directly immobilized on M5 sensor chip. Library Antibodies (Mouse IgG2a) diluted to 1 ug/ml to reach approximately 20-50 RU. Antigens (scFV Fc Fusions) are associated at 500 nM to 0.8 nM, 1:5 dilutions for 3 minutes. Dissociation for 30 mins. The result of the assay (Table 2 below) shows similar binding affinity to KLB513 as what was seen using the ProteOn Binding Assay Using Soluble Proteins with Proteon and Biacore ProteOn XPR36 system (BioRad) was used to perform binding assays. ProteOn GLC chips (BioRad, Cat #176-5011) were coated with Anti-Mouse Fc antibody. Library Antibodies (Mouse IgG2a) were diluted to 0.25 ug/ml to 1 ug/ml to reach approximately 100-200RL. Antigens (scFv-Fc Fusions) were associated at 1000 nM to 0.4 nM, 1:4 dilutions for 3 minutes, followed by dissociation for 30 mins. The results of the assay (Table 1 below) show similar binding affinity of A002B39 with both KLB513 and KLB610.

TABLE 1

Proteon binding results for A002B39 to KLB513 and KLB610.

| | Proteon Binding to KL2B513.002 | | | Proteon Binding to KL2B610.002 | | |
|---|---|---|---|---|---|---|
| Protein AA Name | ka 1/Ms | kd 1/s | KD M | ka 1/Ms | kd 1/s | KD M |
| A002B39 | 3.39E+05 | 3.33E−04 | 9.90E−10 | 2.85E+05 | 3.15E−04 | 1.11E−09 |

Anti-Mouse Fc antibody directly immobilized on M5 sensor chip. Library Antibodies (Mouse IgG2a) diluted to 1 ug/ml to reach approximately 40-80 RU. Antigens (scFV Fc Fusions) are associated at 500 nM to 0.8 nM, 1:5 dilutions for 3 minutes. Dissociation for 30 mins. The results of the assay (Table 2 below) show the binding affinity of A002B39 with KLB513.

TABLE 2

Biacore binding results for A002B39 to KLB513.

| | Biacore Binding to KL2B513.002 | | |
|---|---|---|---|
| Protein AA Name | ka 1/Ms | kd 1/s | KD M |
| A002B39 | 5.79E+04 | 2.02E−04 | 3.49E−09 |

Cell Binding Assay

ScFv transfected SupT1-KL2B413 HL, SupT1-KL2B413 LH or SupT1-CD9B337-HL cells were cultured in RMPI 1640, 10% FBS, 1% Non-Essential Amino Acids, 1 mM Sodium Pyruvate, 2 mM L-glutamine, 10 mM HEPES, 0.1% bicarbonate. Cell culture supplements were ThermoFisher Scientific Gibco products. The mAbs were diluted to 6 micrograms/mL in Stain Buffer (BSA) (BD Pharmingen cat #554657). ScFv expressing SupT1 cells were labeled with fixable Live/Dead stain (Molecular Probes #L34974) and added to a 384-well V-bottom microplate (Greiner Bio-One #781281) at 50,000 cells/well.

The normalized mAb samples were added in 20 ul/well volume to the cell suspensions with gentle mixing and the cells incubated on ice for 30 min. The cell suspension was diluted with 70 ul/well ice cold Stain Buffer (BSA), cells pelleted at 400×g for 5 min at 4° C. and the supernatant aspirated. The cell pellets were washed once more with 70 ul/well ice cold Stain Buffer (BSA). 3 ug/ml of AF488 anti-mouse IgG (H+L) specific goat F(ab')$_2$ (Jackson ImmunoResearch #115-546-062) was added to the cell pellets at 40 ul/well with gentle mixing and the cells incubated on ice, in the dark, for 30 min. The cells were washed as already described and fixed with 40 ul/well BD Cytofix (BD Pharmingen #554655) for 20 min on ice. The fixed cells were washed as described above and the cell pellets resuspended in 20 ul Stain Buffer and analyzed on an iQue PLUS VBR flow cytometer. Cells were gated on live and singlet populations and analyzed for antibody binding in the BL1-H (AF488) channel. All liquid handling was performed on an Agilent Bravo system and aspiration of 384-well plates were handled on a BioTek 405 Select plate washer.

Figure 3:
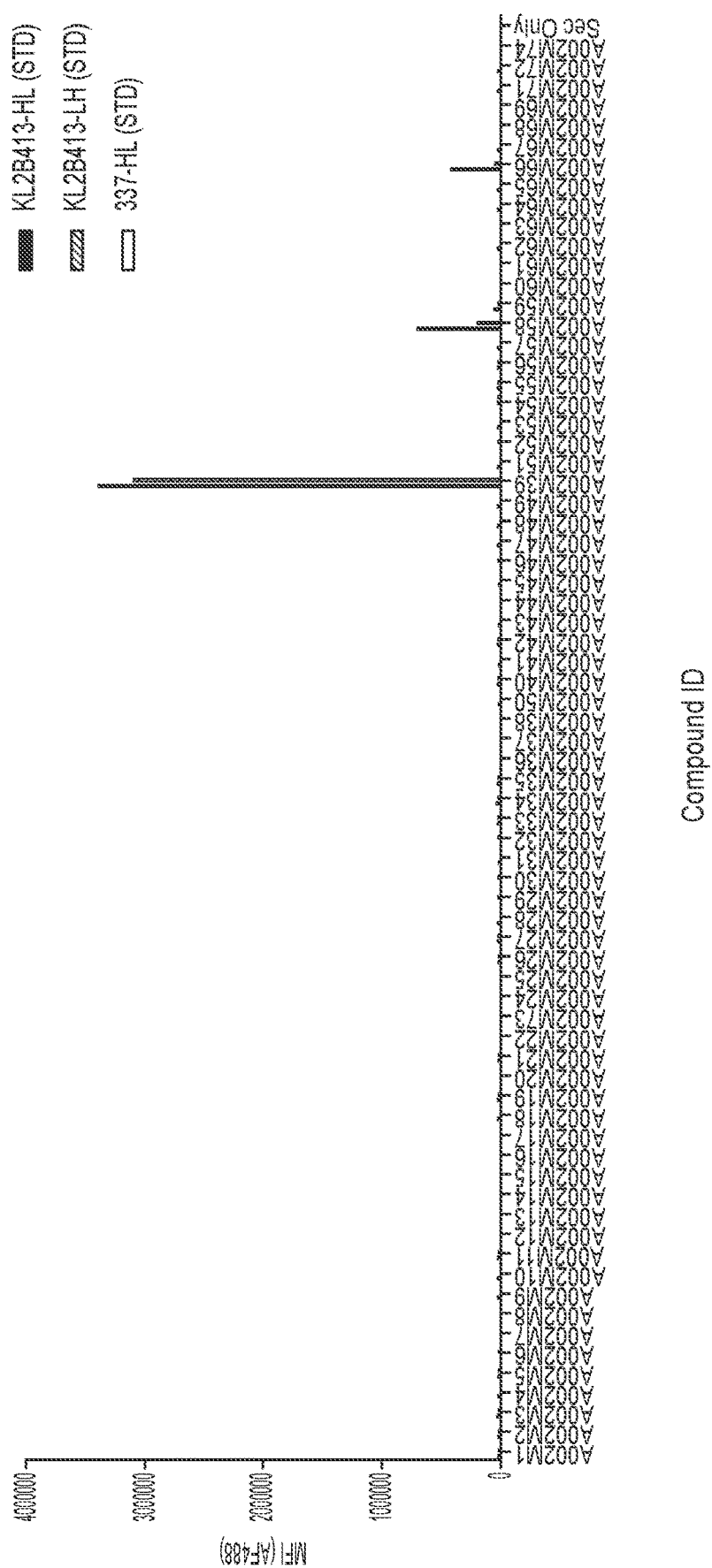
FIG. 3 shows a graphical representation of a cell based binding assay where monoclonal antibodies were screened in binding to scFv-transfected SupT1 cells.

As shown in FIG. 3, a number of candidate mAbs were screened in binding to scFv-transfected SupT1 cells. A002B39 (labeled as A002M39) showed specific binding to both SupT1-KL2B413 HL, SupT1-KL2B413 LH cells and not to the negative control SupT1-CD9B337-HL.

Example 4: Characterization of Detection Antibodies for KLK2 CAR KL2B413-LH (Protein ID #A002B39) on CAR+ SupT1 Cells Antibodies to detect KLK2 CAR (KL2B413-LH) expressed on NK and T cells were identified from panels of proteins derived from Phage Display screening. As discussed in the preceding examples, the proteins were tested initially for binding to recombinant CAR protein and potential binders were scaled up. The proteins were purified and tested for dose dependent binding to SupT1 cells expressing KL2B413-LH respectively by flow cytometry. The binding was determined to be specific to CAR through competition binding experiments with Fc-KL2B413-LH fusion proteins and through lack of binding to parental SupT1 cells. After selection of the best binder, the antibodies were directly conjugated to recombinant phycoerythrin ("PE") for use as CAR detection reagents. The antibodies were purified to a 1:1 PE:antibody ratio to enable receptor enumeration studies (number of CAR expressed on the cell surface).

Purification

Cell culture supernatant was loaded to a MabSelect column and eluted with low pH buffer such as 100 mM sodium acetate pH 3.0, subsequently buffer exchanged to 1×SSC, 8.5% sucrose pH 7.0 using a Sephadex G-25 column. Fractions containing protein were collected. Following purification, proteins underwent QC using SDS-PAGE, SEC-HPLC and LC-MS methods.

Phycoerythrin Labeling

1 μL of Modifier reagent was added to each 10 μL of antibody to be labeled and mixed gently. The antibody sample (with added Modifier reagent) was pipetted directly onto the lyophilized PE (Expedeon, Cat #703-0015), then resuspended gently and incubated for 1 hour in the dark at room temperature (20-25° C.). 1 μL of Quencher reagent was added for every 10 μL of antibody used and incubated for 30 minutes.

After labeling, PE-antibody conjugates were purified on a size-exclusion chromatogram column. Fractions were collected and analyzed on SEC-HPLC. Fractions that only contained one antibody with one PE were pooled together and concentrated if necessary. Final products were analyzed on SEC-HPLC.

Characterization of KLK2 CAR (KL2B413-LH) Anti-Idiotypic Antibody A002B39

Figure 4:
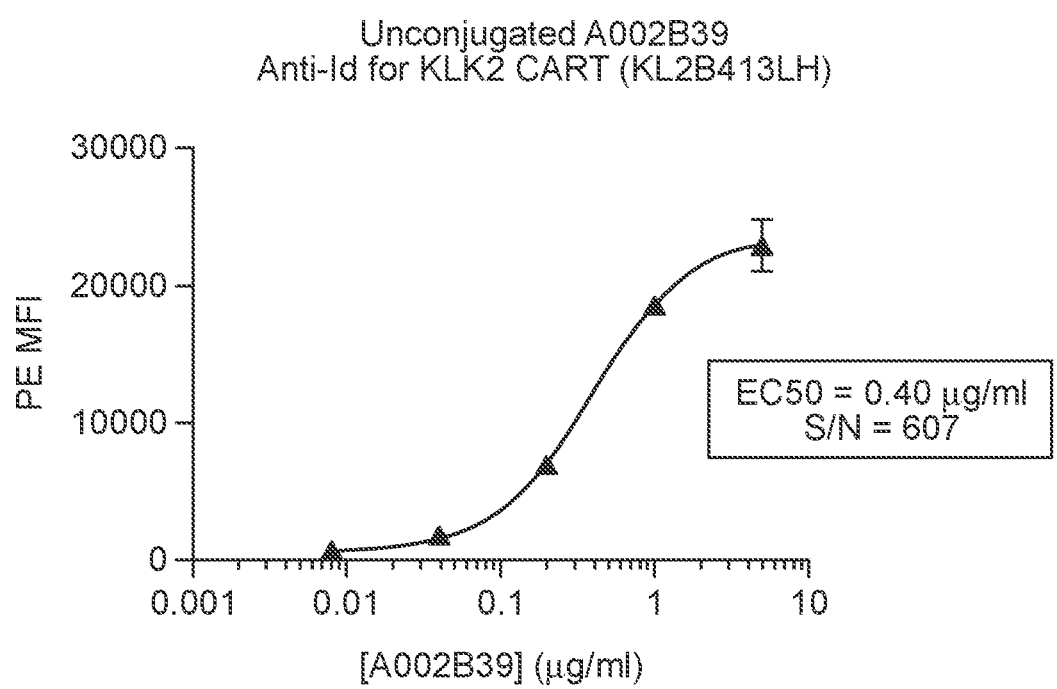
FIG. 4 shows a graphical representation of dose dependent binding of A002B39 to KL2B413-LH SupT1 cells.

SupT1 cells expressing KL2B413LH were compared to parental CAR– SupT1 cells. Cells (100,000 cells/well) were stained with LIVE/DEAD Fixable Near-IR viability dye (Life Technologies L10119) and then incubated with increasing concentrations of A002B39 for 30 minutes on ice. Following incubation, the samples were washed with BSA stain buffer (BD Biosciences #554657) and stained with PE-goat anti-mouse IgG polyclonal antibody (Biolegend #405307) to detect bound antibody on live CAR+ SupT1 cells. After incubation, washing, and fixation (Cytofix, BD Biosciences), the samples were acquired on a 10 color FACSCanto II (BD Biosciences) flow cytometer. Analysis was done using FlowJo and the PE median fluorescent intensity of live SupT1 cells is plotted in FIG. 4. As shown in FIG. 4, dose dependent binding of A002B39 to KL2B413-LH SupT1 cells was observed. No binding was detected on CAR– SupT1 parental cells.

Figure 5:
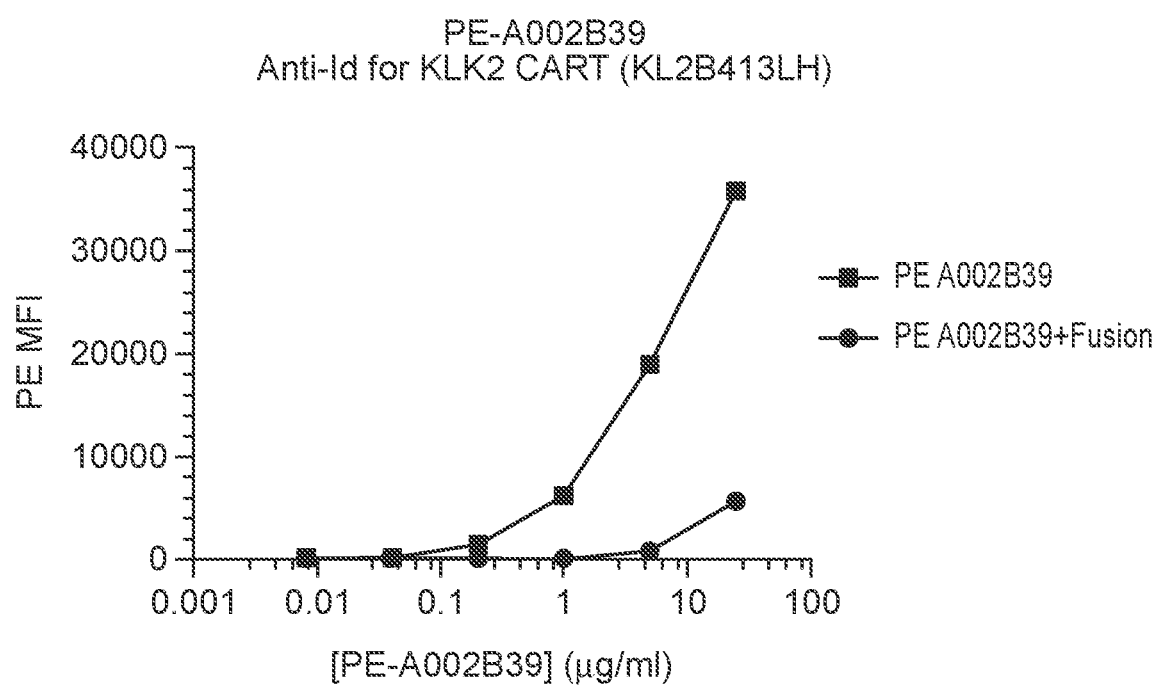
FIG. 5 shows a graphical representation of blocking the dose dependent binding of PE-A002B39 to KL2B413-LH SupT1 cells with KL2B413-LH scFv-Fc fusion protein.

A002B39 was conjugated to R-PE as described above and tested for binding to KL2B413-LH SupT1 in the presence or absence of 10 pg/mL KL2B413-LH scFv Fc fusion protein to assess the specificity of A002B39 binding to KL2B413 CAR. KL2B413-LH SupT1 cells (100,000 cells/well) were stained with LIVE/DEAD Fixable Near-IR viability dye (Life Technologies L10119) and then incubated with increasing concentrations of PE-A002B39 and 10 pg/mL KL2B413-LH scFv Fc for 30 minutes on ice. After incubation, washing, and fixation, the samples were acquired on a 10 color FACSCanto II flow cytometer. Analysis was performed using FlowJo analysis software and the PE median fluorescent intensity of live SupT1 cells is plotted in FIG. 5. As shown in FIG. 5, dose dependent binding of PE-A002B39 to KL2B413-LH SupT1 cells is specific to KL2B413-LH CAR and can be blocked by 10 pg/mL KL2B413-LH scFv-Fc.

Figure 6:
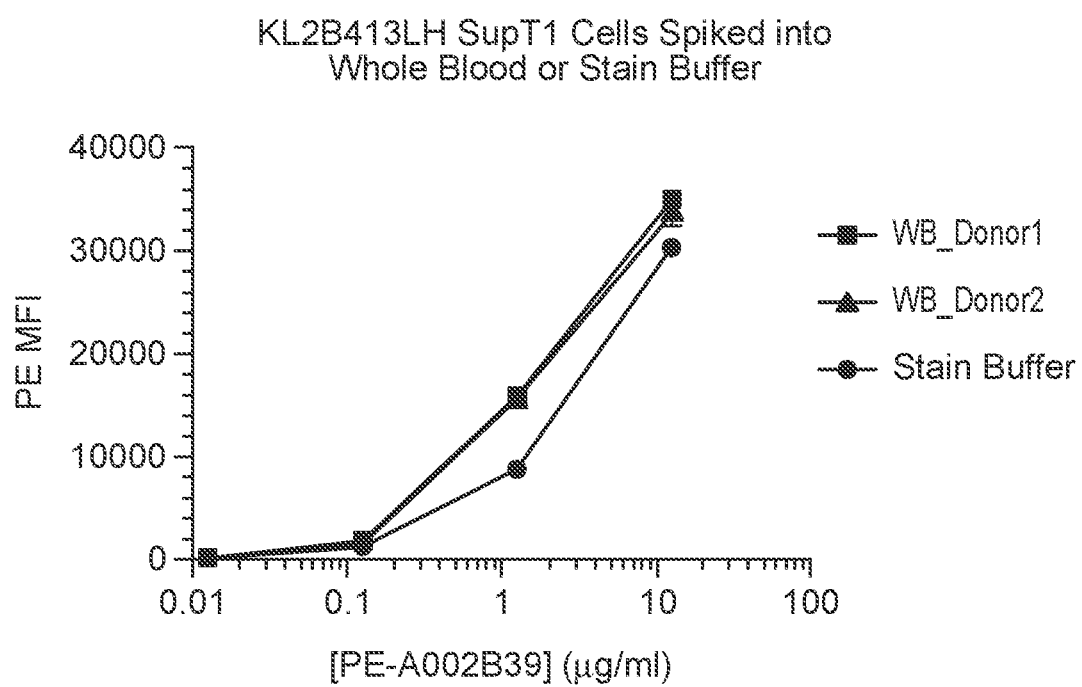
FIG. 6 shows a graphical representation of PE-A002B39 detection of KL2B413-LH-SupT1 cells spiked in whole blood.

KL2B413LH SupT1 cells were spiked into whole blood in order to mirror detection of CAR cells in clinical samples. As shown below in FIG. 3, KL2B413-LH CAR detection by PE-A002B39 was not inhibited in the presence of whole blood. KL2B413LH SupT1 cells were stained with LIVE/DEAD Fixable Near-IR viability dye, washed, and suspended in stain buffer or fresh whole blood (n=2) so that 100,000 KL2B413LH SupT1 cells was plated in 50 μL/well and incubated with increasing concentrations of PE-A002B39 for 30 minutes on ice. After incubation, washing, and fixation, the samples were acquired on a 10 color FACSCanto II flow cytometer. Analysis was done using FlowJo software and the PE median flurorescent intensity of live SupT1 cells is plotted in FIG. 6. As shown in FIG. 6, PE-A002B39 detection of KL2B413-LH-SupT1 cells spiked in whole blood.

Multiple lots of PE-A002B39 were compared to assess differences in binding to KL2B413LH-SupT1 cells across batches. KL2B413-LH SupT1 cells (200,000 cells/well) were stained with LIVE/DEAD Fixable Near-IR viability dye and incubated with increasing concentrations of PE-A002B39 for 30 minutes on ice. After incubation, washing, and fixation, the samples were acquired on a 10 color FACSCanto II flow cytometer. Analysis was done using FlowJo analysis software and the PE median fluorescent intensity of live SupT1 cells is plotted in FIG. 7. As shown in FIG. 7, two different lots of PE-A002B39 have similar binding profiles to KL2B413-LH-SupT1.

Sequences

TABLE 3

CDR and Framework Sequences

| SEQ ID NO. | Region | Definition | Sequence Fragment | Residues | Length |
|---|---|---|---|---|---|
| \multicolumn{6}{c}{VH CDR and framework} |

| SEQ ID NO. | Region | Definition | Sequence Fragment | Residues | Length |
|---|---|---|---|---|---|
| 1 | HFR1 | Chothia | EVQLVQSGAEVKKPGSSVKVSCKAS----- | 1-25 | 25 |
| 1 |  | AbM | EVQLVQSGAEVKKPGSSVKVSCKAS----- | 1-25 | 25 |
| 2 |  | Kabat | EVQLVQSGAEVKKPGSSVKVSCKASGGTFS | 1-30 | 30 |
| 3 |  | Contact | EVQLVQSGAEVKKPGSSVKVSCKASGGTF- | 1-29 | 29 |
| 4 | CDR-H1 | Chothia | GGTFSSY--- | 26-32 | 7 |
| 5 |  | AbM | GGTFSSYAIS | 26-35 | 10 |
| 6 |  | Kabat | -----SYAIS | 31-35 | 5 |
| 7 |  | Contact | ----SSYAIS | 30-35 | 6 |
| 8 | HFR2 | Chothia | AISWVRQAPGQGLEWMGGI | 33-51 | 19 |
| 9 |  | AbM | ---WVRQAPGQGLEWMG-- | 36-49 | 14 |
| 9 |  | Kabat | ---WVRQAPGQGLEWMG-- | 36-49 | 14 |
| 10 |  | Contact | ---WVRQAPGQGLE----- | 36-46 | 11 |
| 11 | CDR-H2 | Chothia | -----IPIFGT--------- | 52-57 | 6 |
| 12 |  | AbM | ---GIIPIFGTAN------- | 50-59 | 10 |
| 13 |  | Kabat | ---GIIPIFGTANYAQKFQG | 50-66 | 17 |
| 14 |  | Contact | WMGGIIPIFGTAN------- | 47-59 | 13 |
| 15 | HFR3 | Chothia | ANYAQKFQGRVTITADESTSTAYMELSSLRSEDTAVYYCAR | 58-98 | 41 |
| 16 |  | AbM | --YAQKFQGRVTITADESTSTAYMELSSLRSEDTAVYYCAR | 60-98 | 39 |
| 17 |  | Kabat | ---------RVTITADESTSTAYMELSSLRSEDTAVYYCAR | 67-98 | 32 |
| 18 |  | Contact | --YAQKFQGRVTITADESTSTAYMELSSLRSEDTAVYYC-- | 60-96 | 37 |
| 19 | CDR-H3 | Chothia | --VQWGLDY | 99-105 | 7 |
| 19 |  | AbM | --VQWGLDY | 99-105 | 7 |
| 19 |  | Kabat | --VQWGLDY | 99-105 | 7 |
| 20 |  | Contact | ARVQWGLD- | 97-104 | 8 |
| 21 | HFR4 | Chothia | -WGQGTLVTVSS | 106-116 | 11 |
| 21 |  | AbM | -WGQGTLVTVSS | 106-116 | 11 |
| 21 |  | Kabat | -WGQGTLVTVSS | 106-116 | 11 |
| 22 |  | Contact | YWGQGTLVTVSS | 105-116 | 12 |
| \multicolumn{6}{c}{VL CDR and framework} |
| 23 | LFR1 | Chothia | EIVLTQSPATLSLSPGERATLSC------ | 1-23 | 23 |
| 23 |  | AbM | EIVLTQSPATLSLSPGERATLSC------ | 1-23 | 23 |
| 23 |  | Kabat | EIVLTQSPATLSLSPGERATLSC------ | 1-23 | 23 |
| 24 |  | Contact | EIVLTQSPATLSLSPGERATLSCRASQSV | 1-29 | 29 |
| 25 | CDR-L1 | Chothia | RASQSVDSALA-- | 24-34 | 11 |
| 25 |  | AbM | RASQSVDSALA-- | 24-34 | 11 |
| 25 |  | Kabat | RASQSVDSALA-- | 24-34 | 11 |
| 26 |  | Contact | ------DSALAWY | 30-36 | 7 |
| 27 | LFR2 | Chothia | WYQQKPGQAPRLLIY | 35-49 | 15 |
| 27 |  | AbM | WYQQKPGQAPRLLIY | 35-49 | 15 |
| 27 |  | Kabat | WYQQKPGQAPRLLIY | 35-49 | 15 |
| 28 |  | Contact | --QQKPGQAPR---- | 37-45 | 9 |
| 29 | CDR-L2 | Chothia | ----GASNRAT | 50-56 | 7 |
| 29 |  | AbM | ----GASNRAT | 50-56 | 7 |
| 29 |  | Kabat | ----GASNRAT | 50-56 | 7 |
| 30 |  | Contact | LLIYGASNRA- | 46-55 | 10 |
| 31 | LFR3 | Chothia | -GIPARFSGSGSGTDFTLTISSLEPEDFAVYYC | 57-88 | 32 |
| 31 |  | AbM | -GIPARFSGSGSGTDFTLTISSLEPEDFAVYYC | 57-88 | 32 |
| 31 |  | Kabat | -GIPARFSGSGSGTDFTLTISSLEPEDFAVYYC | 57-88 | 32 |
| 32 |  | Contact | TGIPARFSGSGSGTDFTLTISSLEPEDFAVYYC | 56-88 | 33 |
| 33 | CDR-L3 | Chothia | QQRFNWPIT | 89-97 | 9 |
| 33 |  | AbM | QQRFNWPIT | 89-97 | 9 |
| 33 |  | Kabat | QQRFNWPIT | 89-97 | 9 |
| 34 |  | Contact | QQRFNWPI- | 89-96 | 8 |
| 35 | LFR4 | Chothia | -FGQGTKVEIK | 98-107 | 10 |
| 35 |  | AbM | -FGQGTKVEIK | 98-107 | 10 |

TABLE 3-continued

CDR and Framework Sequences

| SEQ ID NO. | Region | Definition | Sequence Fragment | Residues | Length |
|---|---|---|---|---|---|
| 35 | | Kabat | -FGQGTKVEIK | 98-107 | 10 |
| 36 | | Contact | TFGQGTKVEIK | 97-107 | 11 |

SEQ ID No. 37: Heavy Chain of A002B39 with muIgG2a (amino acid)
EVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARVQ
WGLDYWGQGTLVTVSSAKTTAPSVYPLAPVCGDTTGSSVTLGCLVKGYFP
EPVTLTWNSGSLSSGVHTFPAVLQSDLYTLSSSVTVTSSTWPSQSITCNV
AHPASSTKVDKKIEPRGPTIKPCPPCKCPAPNLLGGPSVFIFPPKIKDVL
MISLSPIVTCVVVDVSEDDPDVQISWFVNNVEVHTAQTQTHREDYNSTLR
VVSALPIQHQDWMSGKEFKCKVNNKDLPAPIERTISKPKGSVRAPQVYVL
PPPEEEMTKKQVTLTCMVTDFMPEDIYVEWTNNGKTELNYKNTEPVLDSD
GSYFMYSKLRVEKKNWVERNSYSCSVVHEGLHNHHTTKSFSRTPGK SEQ ID No. 38: Heavy Chain of A002B39 with muIgG2a (DNA)
GAAGTGCAGCTGGTGCAGAGCGGCGCGGAAGTGAAAAAACCGGGCAGCAG
CGTGAAAGTGAGCTGCAAAGCGAGCGGCGGCACCTTTAGCAGCTATGCGAT
TAGCTGGGTGCGCCAGGCGCCGGGCCAGGGCCTGGAATGGATGGGCGGCAT
TATTCCGATTTTTGGCACCGCGAACTATGCGCAGAAATTTCAGGGCCGCGT
GACCATTACCGCGGATGAAAGCACCAGCACCGCGTATATGGAACTGAGCAG
CCTGCGCAGCGAAGATACCGCGGTGTATTATTGCGCGCGCGTGCAGTGGGG
CTTGGACTATTGGGGCCAGGGCACCCTGGTGACCGTGAGCAGCGCCAAAAC
AACAGCACCAAGGTGTCTATCCACTGGCCCCTGTGTGTGGAGATACAACTGG
CTCCTCGGTGACTCTAGGATGCCTGGTCAAGGGTTATTTCCCTGAGCCAGT
GACCTTGACCTGGAACTCTGGATCCCTGTCCAGTGGTGTGCACACCTTCCC
AGCTGTCCTGCAGTCTGACCTCTACACCCTCAGCAGCTCAGTGACTGTAAC
CTCGAGCACCTGGCCCAGCCAGTCCATCACCTGCAATGTGGCCCACCCGGC
AAGCAGCACCAAGGTGGACAAGAAAATTGAGCCCAGAGGGCCCACAATCAA
GCCCTGTCCTCCATGCAAATGCCCAGCACCTAACCTCTTGGGTGACCATC
CGTCTTCATCTTCCCTCCAAAGATCAAGGATGTACTCATGATCTCCCTGAG
CCCCATAGTCACATGTGTGGTGGTGGATGTGAGCGAGGATGACCCAGATGT
CCAGATCAGCTGGTTTGTGAACAACGTGGAAGTACACAGCTCAGACACA
AACCCATAGAGAGGATTACAACAGTACTCTCCGGGTGGTCAGTGCCCTCCC
CATCCAGCACCAGGACTGGATGAGTGGCAAGGAGTTCAAATGCAAGGTCAA
CAACAAAGACCTCCCAGCGCCCATCGAGAGAACCATCTCAAAACCCAAAGG
GTCAGTAAGAGCTCCAGGGTATATGTCTTGCCTCCACCAGAAGAAGAGAT
GACTAAGAAACAGGTCACTCTGACCTGCATGGTCACAGACTTCATGCCTGA
AGACATTTACGTGGAGTGGACCAACAACGGGAAAACAGAGCTAAACTACAA
GAACACTGAACCAGTCCTGGACTCTGATGGTTCTTACTTCATGTACAGCAA
GCTGAGAGTGGAAAAGAAGAACTGGGTGGAAAGAAATAGCTACTCCTGTTC
AGTGGTCCACGAGGGTCTGCACAATCACCACACGACTAAGAGCTTCTCCCG
GACTCCGGGTAAA SEQ ID No. 39: Light Chain of A002B39 with muKappa (amino acid)
EIVLTQSPATLSLSPGERATLSCRASQSVDSALAWYQQKPGQAPRLLIYGA
SNRATGIPARFSGSGSGTDFTLTISSLEPEDFAVYYCQQRFNWPITFGQGT
KVEIKRADAAPTVSIFPPSSEQLTSGGASVVCFLNNFYPKDINVKWKIDGS
ERQNGVLNSWTDQDSKDSTYSMSSTLTLTKDEYERHNSYTCEATHKTSTSP
IVKSFNRNEC SEQ ID No. 40: Light Chain of A002B39 with muKappa (DNA)
GAAATTGTGCTGACCCAGAGCCCGGCGACCCTGAGCCTGAGCCCGGGCGAA
CGCGCGACCCTTAGCTGCCGTGCAAGTCAGAGTGTGGACAGCGCGCTGGCG
TGGTATCAGCAGAAACCGGGCCAGGCGCCGCGCCTGCTGATTTATGGTGCG
AGCAACCGCGCGACCGGCATTCCGGCGCGCTTTAGCGGCAGCGGCAGCGGC
ACCGATTTTACCCTGACCATTAGCAGCCTGGAACCGGAAGATTTTGCGGTG
TATTATTGCCAGCAGCGTTTCAACTGGCCGATCACCTTTGGCCAGGGCACC
AAAGTGGAAATTAAACGGGCTGATGCTGCACCGACTGTGTCCATCTTCCCA
CCATCCAGTGAGCAGTTAACATCTGGAGGTGCCTCAGTCGTGTGCTTCTTG
AACAACTTCTACCCCAAAGACATCAATGTCAAGTGGAAGATTGATGGCAGT
GAACGACAAAATGGCGTCCTGAACAGTTGGACTGATCAGGACAGCAAAGAC
AGCACCTACAGCATGAGCAGCACCCTCACGTTGACCAAGGACGAGTATGAA
CGACATAACAGCTATACCTGTGAGGCACTCACAAGACATCAACTTCACCC
ATTGTCAAGAGCTTCAACAGGAATGAGTGT SEQ ID No. 41: KL2B413 VH
EVQLVESGGGLVQPGGSLRLSCAASGFTFSSYWMTWVRQAPGKGLEWVANI
KQDGSERYYVDSVKGRFTISRDNAKNSLYLQMNSLRAEDTAVYYCARDQNY
DILTGHYGMDVWGQGTTVTVSS SEQ ID No. 42: KL2B413 VL
EIVLTQSPSFLSASVGDRVTITCRASQGISSYLSWYQQKPGKAPKLLIYAT
STLQSGVPSRFSGSGSGTEFTLTISSLQPEDFATYYCQQLNSYPRTFGQGT
KVEIK SEQ ID NO: 43 - CAR 1 (KL2B413_HL; pBD000091628)
EVQLVESGGGLVQPGGSLRLSCAASGFTFSSYWMTWVRQAPGKGLEWVANI
KQDGSERYYVDSVKGRFTISRDNAKNSLYLQMNSLRAEDTAVYYCARDQNY -continued

DILTGHYGMDVWGQGTTVTVSSGGSEGKSSGSGSESKSTGGSEIVLTQSPS

FLSASVGDRVTITCRASQGISSYLSWYQQKPGKAPKLLIYATSTLQSGVPS

RFSGSGSGTEFTLTISSLQPEDFATYYCQQLNSYPRTFGQGTKVEIKTSTP

APRPPTPAPTIASQPLSLRPEACRPAAGGAVHTRGLDFACDIYIWAPLAGT

CGVLLLSLVITLYCKRGRKKLLYIFKQPFMRPVQTTQEEDGCSCRFPEEEE

GGCELRVKFSRSADAPAYKQGQNQLYNELNLGRREEYDVLDKRRGRDPEMG

GKPRRKNPQEGLYNELQKDKMAEAYSEIGMKGERRRGKGHDGLYQGLSTAT

KDTYDALHMQALPPR

SEQ ID NO: 44 - CAR 2 (KL2B413 LH; pBD000091623)
EIVLTQSPSFLSASVGDRVTITCRASQGISSYLSWYQQKPGKAPKLLIYAT

STLQSGVPSRFSGSGSGTEFTLTISSLQPEDFATYYCQQLNSYPRTFGQGT

KVEIKGGSEGKSSGSGSESKSTGGSEVQLVESGGGLVQPGGSLRLSCAASG

FTFSSYWMTWVRQAPGKGLEWVANIKQDGSERYYVDSVKGRFTISRDNAKN

SLYLQMNSLRAEDTAVYYCARDQNYDILTGHYGMDVWGQGTTVTVSSTSTP

APRPPTPAPTIASQPLSLRPEACRPAAGGAVHTRGLDFACDIYIWAPLAGT

CGVLLLSLVITLYCKRGRKKLLYIFKQPFMRPVQTTQEEDGCSCRFPEEEE

GGCELRVKFSRSADAPAYKQGQNQLYNELNLGRREEYDVLDKRRGRDPEMG

GKPRRKNPQEGLYNELQKDKMAEAYSEIGMKGERRRGKGHDGLYQGLSTAT

KDTYDALHMQALPPR

SEQ ID No. 45: Heavy Chain Variable Domain of
A002B39 (amino acid)
EVQLVQSGAEVKKPGSSVKVSCKASGGTFSSYAISWVRQAPGQGLEWMGGI

IPIFGTANYAQKFQGRVTITADESTSTAYMELSSLRSEDTAVYYCARVQWG

LDYWGQGTLVTVSS

SEQ ID No. 46: Light Chain Variable Domain of
A002B39 (amino acid)
EIVLTQSPATLSLSPGERATLSCRASQSVDSALAWYQQKPGQAPRLLIYGA

SNRATGIPARFSGSGSGTDFTLTISSLEPEDFAVYYCQQRFNWPITFGQGT

KVEIK

SEQ ID NO: 47 - human Kallikrein-2 sequence
(signal sequence: amino acids 1-18)
MWDLVLSIALSVGCTGAVPLIQSRIVGGWECEKHSQPWQVAVYSHGWAHCG

GVLVHPQWVLTAAHCLKKNSQVWLGRHNLFEPEDTGQRVPVSHSFPHPLYN

MSLLKHQSLRPDEDSSHDLMLLRLSEPAKITDVVKVLGLPTQEPALGTTCY

ASGWGSIEPEEFLRPRSLQCVSLHLLSNDMCARAYSEKVTEFMLCAGLWTG

GKDTCGGDSGGPLVCNGVLQGITSWGPEPCALPEKPAVYTKVVHYRKWIKD

TIAANP

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An anti-idiotype antibody or antigen-binding portion thereof that specifically binds to a target antibody or antigen-binding portion thereof wherein the target antibody comprises a VH domain comprising SEQ ID NO: 41 and a VL domain comprising SEQ ID NO: 42, wherein the anti-idiotype antibody or antigen-binding portion comprises a heavy chain variable (VH) domain comprising a VH CDR1 having an amino acid sequence selected from the group consisting of SEQ ID NOs:4-7, a VH CDR2 having an amino acid sequence selected from the group consisting of SEQ ID NOs:11-14 and a VH CDR3 having an amino acid sequence selected from the group consisting of SEQ ID NOs:19-20, and further comprises a light chain variable (VL) domain comprising a VL CDR1 having an amino acid sequence selected from the group consisting of SEQ ID NOs:25-26, a VL CDR2 having an amino acid sequence selected from the group consisting of SEQ ID NOs:29-30 and a VL CDR3 having an amino acid sequence selected from the group consisting of SEQ ID NO:33-34.

2. The anti-idiotype antibody or antigen-binding portion of claim 1, wherein the anti-idiotype antibody or antigen-binding portion thereof comprises a VH domain comprising SEQ ID NO:45 and a VL domain comprising SEQ ID NO:46.

3. The anti-idiotype antibody or antigen-binding portion of claim 1, wherein the anti-idiotype antibody or antigen-binding portion comprises a heavy chain comprising SEQ ID NO:37 and further comprises a light chain comprising SEQ ID NO:39.

4. The anti-idiotype antibody or antigen-binding portion of claim 1, wherein the anti-idiotype antibody or antigen-binding portion thereof comprises an antigen-binding portion selected from a Fab, F(ab')$_2$, or scFv.

5. The anti-idiotype antibody or antigen-binding portion of claim 1, wherein the anti-idiotype antibody or antigen-binding portion thereof is a monoclonal antibody.

6. The anti-idiotype antibody or antigen-binding portion of claim 1, wherein the anti-idiotype antibody or antigen-binding portion thereof is a chimeric antibody.

7. The anti-idiotype antibody or antigen-binding portion of claim 6, wherein the anti-idiotype antibody or antigen-binding portion thereof comprises a murine IgG2a constant region.

8. The anti-idiotype antibody or antigen-binding portion of claim 1, wherein the anti-idiotype antibody or antigen-binding portion thereof is in a human constant region.

9. A nucleic acid encoding the heavy chain, the light chain, or both, of the anti-idiotype antibody or antigen-binding portion of claim 1.

10. A nucleic acid encoding the heavy chain, the light chain, or both, of an anti-idiotype antibody or an antigen-binding portion thereof that specifically binds KL2B413, wherein said nucleic acid comprises:
 a) the nucleotide sequence of SEQ ID NO: 38;
 b) the nucleotide sequence of SEQ ID NO: 40;
 c) both a) and b).

11. A vector comprising the nucleic acid of claim 10.

12. The vector of claim 11, wherein the vector is an expression vector.

13. A host cell comprising the vector of claim 12.

14. The host cell of claim 13, wherein the cell is a mammalian cell.

15. A method of producing an anti-idiotype antibody or antigen-binding portion thereof that specifically binds KL2B413, said method comprising culturing the host cell of claim 13 under conditions that allow said antibody or antigen-binding portion to be expressed, wherein the host cell comprises nucleotide sequences coding the heavy chain and light chain of the antibody or antigen-binding portion, and isolating said antibody or antigen-binding portion from the culture.

16. A method for detecting KL2B413 in a biologic sample comprising: (a) providing a biological sample; (b) contacting the biological sample with the anti-idiotype antibody or antigen-binding portion of claim 1; and (c) detecting the anti-idiotype antibody or antigen-binding portion, wherein the KL2B413 comprises a VH domain comprising SEQ ID NO: 41 and a VL domain comprising SEQ ID NO: 42.

17. A method for detecting expression of a chimeric antigen receptor (CAR) comprising KL2B413 in a biologic sample comprising: (a) providing a biological sample; (b) contacting the biological sample with the anti-idiotype antibody or antigen-binding portion of claim 1; and (c) detecting the anti-idiotype antibody or antigen-binding portion, and thereby detecting the expression of the CAR comprising SEQ ID NO: 41 and a VL domain comprising SEQ ID NO: 42.

18. The method according to claim 16, wherein the antibody comprises a detectable label.

19. The method according to claim 16, wherein the method further comprises contacting the anti-idiotype antibody or antigen-binding portion with a detectable label before detecting the anti-idiotype antibody or antigen-binding portion.

20. The method according to claim 16, wherein the biological sample is blood, serum or urine.

21. The anti-idiotype antibody or antigen-binding portion of claim 1, wherein the target antibody or antigen-binding portion thereof is within the antigen-binding domain of the extracellular portion of a chimeric antigen receptor (CAR).

22. The anti-idiotype antibody or antigen-binding portion of claim 21 wherein the target antibody or antigen-binding portion thereof is an scFv and the anti-idiotype antibody or antigen-binding portion specifically binds an epitope in the scFv of the CAR.

23. The anti-idiotype antibody or antigen-binding portion of claim 21, wherein the target antibody or antigen-binding portion thereof binds KLK2.

24. The anti-idiotype antibody or antigen-binding portion of claim 21, wherein the anti-idiotype antibody or antigen-binding portion thereof does not cross-react to other KLK2 antibodies or other KLK2 binding CARs.

25. The anti-idiotype antibody or antigen-binding portion of claim 21, wherein the CAR has an amino acid sequence selected from the group consisting of SEQ ID NOs: 43-44.

26. A kit for detecting the target antibody or antigen-binding portion thereof of claim 1 in a biologic sample comprising: (a) the anti-idiotype antibody or antigen-binding portion of claim 1; and (b) instructions for detecting the target antibody or antigen-binding portion thereof.

27. The anti-idiotype antibody or antigen-binding portion of claim 1, wherein the anti-idiotype antibody or antigen-binding portion detects the target antibody or antigen-binding portion in a biologic sample.

28. A method of purifying KL2B413 from a sample comprising: (a) providing a biological sample comprising KL2B413; (b) contacting the biological sample with the anti-idiotype antibody or antigen-binding portion of claim 1; and (c) capturing the anti-idiotype antibody or antigen-binding portion, and thereby purifying KL2B413 comprising SEQ ID NO: 41 and a VL domain comprising SEQ ID NO: 42.

29. A method of selecting CAR-T cell comprising SEQ ID NO: 43 or 44 from a cell population comprising: (a) providing a biological sample comprising CAR-T cells; (b) contacting the biological sample with the anti-idiotype antibody or antigen-binding portion of claim 1; and (c) capturing the anti-idiotype antibody or antigen-binding portion, and thereby selecting CAR-T cells.

* * * * *